United States Patent
Georgescu

(10) Patent No.: US 12,243,231 B2
(45) Date of Patent: Mar. 4, 2025

(54) COMPUTER SUPPORTED REVIEW OF TUMORS IN HISTOLOGY IMAGES AND POST OPERATIVE TUMOR MARGIN ASSESSMENT

(71) Applicant: Leica Biosystems Imaging, Inc., Vista, CA (US)

(72) Inventor: Walter Georgescu, Vista, CA (US)

(73) Assignee: Leica Biosystems Imaging, Inc., Vista, CA (US)

( * ) Notice: Subject to any disclaimer, the term of this patent is extended or adjusted under 35 U.S.C. 154(b) by 0 days.

(21) Appl. No.: 18/543,461

(22) Filed: Dec. 18, 2023

(65) Prior Publication Data

US 2024/0119595 A1 Apr. 11, 2024

Related U.S. Application Data

(63) Continuation of application No. 17/415,396, filed as application No. PCT/US2020/035286 on May 29, 2020, now Pat. No. 11,893,732.

(Continued)

(51) Int. Cl.
*G06T 7/00* (2017.01)
*G06F 18/214* (2023.01)
(Continued)

(52) U.S. Cl.
CPC ........ *G06T 7/0012* (2013.01); *G06F 18/2148* (2023.01); *G06F 18/24* (2023.01);
(Continued)

(58) Field of Classification Search
None
See application file for complete search history.

(56) References Cited

U.S. PATENT DOCUMENTS 10,169,685 B2 * 1/2019 Chen ....................... G06T 7/187
10,705,088 B2 * 7/2020 Dakappagari ........... A61P 37/04
(Continued)

FOREIGN PATENT DOCUMENTS

EP 2733669 A2 5/2014

OTHER PUBLICATIONS

Araújo, Flavio HD, et al. "Deep learning for cell image segmentation and ranking." Computerized Medical Imaging and Graphics 72 (2019): 13-21 cited in IDS and provided (Year: 2019).*

(Continued)

*Primary Examiner* — Anand P Bhatnagar
(74) *Attorney, Agent, or Firm* — FROST BROWN TODD LLP

(57) ABSTRACT

A computer apparatus and method for identifying and visualizing tumors in a histological image and measuring a tumor margin are provided. A CNN is used to classify pixels in the image according to whether they are determined to relate to nontumorous tissue, or one or more classes for tumorous tissue. Segmentation is carried out based on the CNN results to generate a mask that marks areas occupied by individual tumors. Summary statistics for each tumor are computed and supplied to a filter which edits the segmentation mask by filtering out tumors deemed to be insignificant. Optionally, the tumors that pass the filter may be ranked according to the summary statistics, for example in order of clinical relevance or by a sensible order of review for a pathologist. A visualization application can then display the histological image having regard to the segmentation mask, summary statistics and/or ranking. Tumor masses extracted by resection are painted with an ink to highlight its surface region. The CNN is trained to distinguish ink and no-ink tissue as well as tumor and no-tumor tissue. The CNN is applied to the histological image to generate an output (Continued)

image whose pixels are assigned to the tissue classes. Tumor margin status of the tissue section is determined by the presence or absence of tumor-and-ink classified pixels. Tumor margin involvement and tumor margin distance are determined by computing additional parameters based on classification-specified inter-pixel distance parameters.

12 Claims, 11 Drawing Sheets

Related U.S. Application Data

(60) Provisional application No. 62/854,055, filed on May 29, 2019, provisional application No. 62/854,014, filed on May 29, 2019.

(51) Int. Cl.
| | |
|---|---|
| *G06F 18/24* | (2023.01) |
| *G06N 3/08* | (2023.01) |
| *G06V 10/94* | (2022.01) |
| *G06V 20/69* | (2022.01) |
| *G16H 30/40* | (2018.01) |
| *G06F 3/04842* | (2022.01) |

(52) U.S. Cl.
CPC ............... *G06N 3/08* (2013.01); *G06V 10/95* (2022.01); *G06V 20/693* (2022.01); *G06V 20/695* (2022.01); *G06V 20/698* (2022.01); *G16H 30/40* (2018.01); *G06F 3/04842* (2013.01); *G06T 2200/24* (2013.01); *G06T 2207/10056* (2013.01); *G06T 2207/20081* (2013.01); *G06T 2207/20084* (2013.01); *G06T 2207/30024* (2013.01); *G06T 2207/30096* (2013.01); *G06V 2201/03* (2022.01)

(56) References Cited

U.S. PATENT DOCUMENTS

| | | | | |
|---|---|---|---|---|
| 11,348,239 | B2 * | 5/2022 | Yip | ...................... G06V 20/698 |
| 11,348,661 | B2 * | 5/2022 | Yip | ........................ G06N 3/045 |
| 11,527,323 | B2 * | 12/2022 | Michuda | ................ G16B 30/00 |
| 11,682,192 | B2 * | 6/2023 | Chukka | ................ G06V 10/774 |
| | | | | 382/128 |
| 2017/0147908 | A1 * | 5/2017 | Chen | ................... G06F 18/2415 |
| 2017/0278669 | A1 * | 9/2017 | Fujiyoshi | ................ H01J 37/22 |
| 2020/0342597 | A1 * | 10/2020 | Chukka | ................ G06V 20/698 |
| 2020/0365268 | A1 * | 11/2020 | Michuda | ................ G16H 50/20 |
| 2021/0142904 | A1 * | 5/2021 | Michuda | ................ G16H 50/20 |
| 2022/0076410 | A1 * | 3/2022 | Georgescu | ............ G06T 7/0012 |
| 2023/0187070 | A1 * | 6/2023 | Michuda | ................ G16H 10/40 |
| | | | | 702/19 |

OTHER PUBLICATIONS

Aperio GT 450, screenshot of Google image search results, accessed on Jan. 17, 2019.
Araújo, Flávio HD, et al. "Deep learning for cell image segmentation and ranking." *Computerized Medical Imaging and Graphics* 72 (2019): 13-21.
Gupta, Anindya, et al. "Deep learning in image cytometry: a review." *Cytometry Part A* 95.4 (2019): 366-380.
Leica Biosystems: "Leica Aperio GT 450 RUO", uploaded Jul. 30, 2019, retrieved from the internet <https://vimeo.com/350887835>, accessed Sep. 8, 2022.
Li, Jiayun, et al. "A multi-scale u-net for semantic segmentation of histological images from radical prostatectomies." *AMIA Annual Symposium Proceedings.* vol. 2017. American Medical Informatics Association, 2017.
Tokunaga, Hiroki, et al. "Adaptive weighting multi-field-of-view CNN for semantic segmentation in pathology." *Proceedings of the IEEE/CVF Conference on Computer Vision and Pattern Recognition.* 2019.
International Search Report and Written Opinion dated Oct. 28, 2020, for International Application No. PCT/US2020/035286, 16 pages.

* cited by examiner

COMPUTER SUPPORTED REVIEW OF TUMORS IN HISTOLOGY IMAGES AND POST OPERATIVE TUMOR MARGIN ASSESSMENT

This is a continuation of U.S. patent application Ser. No. 17/415,396, entitled "Computer Supported Review of Tumors in Histology Images and Post Operative Tumor Margin Assessment," filed Jun. 17, 2021, which is itself a national entry of PCT application PCT.US2020/035286, entitled "Computer Supported Review of Tumors in Histology Images and Post Operative Tumor Margin Assessment", filed May 28, 2020, which is itself a non-provisional of U.S. provisional patent application 62/854,014, entitled "Computer-Supported Review of Tumors in Histology Images," filed May 29, 2019, and U.S. provisional patent application 62/854,055, entitled "Post-Operative Tumor Margin Assessment," filed May 29, 2019, the disclosures of each which are incorporated by reference herein in their entirety.

BACKGROUND

Field of the Invention

The present disclosure relates to image processing of histology images that contain tumors with a convolutional neural network (CNN) so as to assist review and diagnosis by a pathologist assessing the margins of a tumor mass that has been removed from a patient by resection.

Related Art

Digital pathology continues to change the way pathologists view and diagnose slides. The traditional way for pathologists to examine a slide is to observe a glass slide under a microscope. The pathologist will start by viewing the slide with a low magnification objective. When an area with potential diagnostic value is observed, the pathologist will switch to a high magnification objective to look in more detail at that area. Subsequently, the pathologist will switch back to low magnification to continue examining other areas on the slide. This low-high-low magnification viewing sequence may be repeated several times over the slide until a definite and complete diagnosis can be made for the slide.

In the past twenty years, the introduction of digital scanners has changed this workflow. A digital scanner can acquire an image of an entire glass slide, a so-called whole slide image (WSI), and save it as a digital image data file in a largely automated process that does not need a pathologist. The resulting image data file is typically stored in a slide database from where it is available via a clinical network to a pathologist at a viewing workstation with a high-resolution display, the workstation having a visualization application for this purpose.

A more recent development in pathology is that CNN methods have become of increasing research interest. It is becoming increasingly reported that CNN methods are performing as well as, or even better than, pathologists in identifying and diagnosing tumors from histology images.

Wang et al 2016 describes a CNN approach to detect metastasis of breast cancer to the lymph nodes.

US2015213302A1 describes how cellular mitosis is detected in a region of cancerous tissue. After training a CNN, classification is carried out based on an automated nuclei detection system which performs a mitotic count, which is then used to grade the tumor.

Hou et al 2016 processes brain and lung cancer images. Image patches from WSIs are used to make patch-level predictions given by patch-level CNNs.

Liu et al 2017 processes image patches extracted from a gigapixel breast cancer histology image with a CNN to detect and localize tumors by assigning a tumor probability to every pixel in the image.

Bejnordi et al 2017 applies two stacked CNNs to classify tumors in image patches extracted from WSIs of breast tissue stained with a hematoxylin and eosin (H&E) stain. The performance is shown to be good for object detection and segmentation in these pathology images. We further note that Bejnordi et al also provides an overview of other CNN-based tumor classification methods applied to breast cancer samples (see references 10-13).

Esteva et al 2017 applies a deep CNN to analyze skin lesions and classify the lesions according to a tree-structured taxonomy into various malignant types, non-malignant types and non-neoplastic types including the malignant types acrolentiginous melanoma, amelanotic melanoma and lentigo melanoma and the non-malignant types blue nevus, halo nevus and Mongolian spot. An image of a skin lesion (for example, melanoma) is sequentially warped into a probability distribution over clinical classes to perform the classification.

Mobadersany et al 2017 disclose a computational method based on a survival CNN to predict the overall survival of patients diagnosed with brain tumors. Pathology image data from tissue biopsies (histology image data) is fed into the model as well as patient-specific genomic biomarkers to predict patient outcomes. This method uses adaptive feedback to simultaneously learn the visual patterns and molecular biomarkers associated with patient outcomes.

Tumor resection is surgery to remove tumor tissue, typically by removing a part of, or all of, an organ or gland, where partial removal is termed segmental resection. The aim of tumor resection is to remove a tissue mass that contains all of the tumor along with a small quantity of normal tissue around the margins of the tumor.

To check that the resection has completely removed the tumor, the following pathology examination is performed after removal of the tissue mass from the body. The surface of the excised tissue mass is painted with a colored ink. The tissue mass is prepared in various ways to conserve the microscopic tissue structure. The tissue mass is then sliced into thin sections with a microtome. After slicing, further conservation measures for the microscopic tissue structure may be performed. The tissue sections are mounted onto slides. The tissue sections are stained with specialist stains or markers to enhance visibility of the cells in general, e.g. by contrast, or to identify specific types of cells with a marker that is specific to particular gene expressions or associated receptors. For breast cancer tumors, the typical receptors to be targeted would be: ER+, ER−, PR+, PR−, HER2+ and HER2−, where ER stands for estrogen receptor, PR stands for progesterone receptor and HER2 stands for human epidermal growth factor receptor 2.

The traditional way to assess the margins is for a pathologist to examine the stained slides under a microscope and determines if any of the tumor cells are on, or too close to, the inked surface. If tumor cells are found on the ink, the pathologist will report the surgical margins as positive (Lester et al. 2009). Positive margins usually indicate that more surgery is needed to remove more tissue mass. For positive margins the pathologist may also report the extent of margin involvement using sub-classifications such as focal, minimal/moderate and extensive that relate to the amount of encroachment into the margin. If cancer cells are close to the inked surface, but not quite on it, e.g. less than 2 mm, then the pathologist may report the tumor margins as 'close'. If there are no cancer cells on the inked surface (not 'positive'), or close to it (not 'close'), the pathologist will report the margins as 'clear', e.g. margin greater than or equal to 2 mm. For clear or close margins, the pathologist may also report a margin distance which indicates the distance between the inked surface and those tumor cells that are closest to the inked surface. In the case of a positive margin, it may be necessary to perform further surgery to remove the left-over cancerous tissue. Even though reporting margin status accurately is important for subsequent cancer treatment, there is wide variability in the quality of margin status reporting (Persing et al. 2011).

Therefore, what are needed are systems and methods that overcomes these significant problems found in the conventional systems as described above.

SUMMARY

According to one aspect of the disclosure, there is provided a method of identifying tumors in a histological image (or set thereof), the method comprising:
  receiving a histological image including a two-dimensional array of pixels;
  applying a convolutional neural network (CNN) to generate an output image with a two-dimensional array of pixels with a mapping to that of the histology image, the output image being generated by assigning one of a plurality of tissue classes to each pixel, wherein the plurality of tissue classes includes at least one class representing non-tumorous tissue and at least one class representing tumorous tissue;
  generating a segmentation mask from the output image, in which areas occupied by individual tumors are marked;
  computing summary statistics for each tumor; and
  applying a filter to the summary statistics of each tumor to edit the segmentation mask by selecting and deselecting tumors according to the filter.

With the proposed approach, it is possible to indicate to a pathologist where in the image potential, or potentially significant, tumors are located and thus prompt the pathologist to navigate directly to those areas. In this way, the reliability of analysis can be improved, since tumor-containing areas are less likely to be missed by the pathologist. Moreover, the throughput can be increased, since the pathologist no longer needs to examine the whole slide area to locate tumor regions. The pathologist is also implicitly encouraged to apportion their limited analysis time in a way that takes account of the filtering and ranking that has been made on the basis of the CNN analysis results, thereby providing a better overall allocation of the pathologist's time in studying any particular slide image.

The method may be extended by scoring each tumor according to a scoring algorithm to assign a score to each tumor. Based on the scores, it is possible to rank the tumors, where the ranking order may represent a variety of useful ordering, e.g. to show perceived clinical relevance, or to predict which order a clinician may wish to review the tumors. The ranking may be confined to those tumors that remain after applying the filter. The ranking may be stored, e.g. into a record, as additional metadata associated with the histological image. The histological image may be received from a record stored in a virtual slide library or other database, or directly after acquisition by a digital scanner in which case the method may be carried out by the digital scanner or by a computer apparatus, e.g. one connected to the digital scanner, or from another data source.

A visualization of the histological image may then be created having regard to the edited segmentation mask. The visualization may then be displayed to a user on a display by a visualization application running on a computer apparatus. For example, the visualization may include an overview viewing pane in which the segmentation mask is overlaid on the histological image. Another option for the visualization is for it to include respective overview viewing panes in which the segmentation mask and the histological image are presented adjacent to each other for one-to-one comparison, e.g. side-by-side. The overview viewing pane(s) may include a ranking label for each tumor based on the ranking. A user interface tumor selection control may be provided to permit a user to interact with the visualization so as to select a tumor in the edited segmentation mask. The visualization may include a close-up viewing pane zoomed in on the currently selected tumor. The tumor selection control may incorporate a scroll function for sweeping through the tumors in the edited segmentation mask in order of ranking. The tumor selection control may also incorporate a diagnostic function for allowing a user to run an additional computational diagnostic process on the currently selected tumor.

In its simplest form, the CNN has only two tissue classes, one for tumorous tissue and one for non-tumorous tissue. However, two or more classes for tumorous tissue may be provided. For example, the tissue classes for tumorous tissue may distinguish between invasive tumors and in situ tumors. There may be only one tissue class for non-tumorous tissue, or multiple classes, e.g. to distinguish bone from other tissue. There may also be a class for non-tissue, i.e. for areas on the whole slide image where there is no sample present as may in particular be useful for tissue microarray samples.

The method may further comprise, after the assigning step, the step of: assembling the output image patches into a probability map for the histological image (or set thereof).

The method may further comprise, after the assembling step, the step of: storing the probability map, e.g. into a record in a data repository, so that the probability map is linked to the histological image (or set thereof).

In our current implementation, in each successive convolution stage, as the dimensions decrease, the depth increases, so that the convolution layers are of ever increasing depth as well as ever decreasing dimensions, and in each successive transpose convolution stage, as the dimensions increase, the depth decreases, so that the deconvolution layers are of ever decreasing depth as well as ever increasing dimensions. The final convolution layer then has a maximum depth as well as minimum dimensions. Instead of the approach of successive depth increases and decreases through respectively the convolution and deconvolution stages, an alternative would be to design a neural network in which every layer except the input layer and the output layer has the same depth.

The method may further comprise: displaying on a display the histological image (or set thereof) with the probability map, e.g. overlaid thereon or alongside each other. The probability map can be used to determine which areas should be scored by whatever immunohistochemistry scoring algorithms are to be used. The probability map can also be used to generate a set of contours around tumor cells which can be presented in the display, e.g. to allow a pathologist to evaluate the results generated by the CNN.

In certain embodiments, the convolutional neural network has one or more skip connections. Each skip connection takes intermediate results from at least one of the convolution layers of larger dimensions than the final convolution layer and subjects those results to as many transpose convolutions as needed, which may be none, one or more than one, to obtain at least one further recovered layer matched in size to the input image patch. These are then combined with the above-mentioned recovered layer prior to said step of assigning a tissue class to each pixel. A further processing step combines the recovered layer with each of the further recovered layers in order to recompute the probabilities, thereby taking account of the results obtained from the skip connections.

In certain embodiments, a softmax operation is used to generate the probabilities.

The image patches extracted from the histological image (s) may cover the whole area of the image(s). The patches may be non-overlapping image tiles or image tiles that overlap at their margins to aid stitching of the probability map. While each image patch should have a fixed number of pixels in width and height to be matched to the CNN, since the CNN will be designed to accept only a fixed size of pixel array, this does not mean that each image patch must correspond to the same physical area on the histological image, because pixels in the histological image may be combined into a lower resolution patch covering a larger area, e.g. each 2×2 array of neighboring pixels may be combined into one 'super'-pixel to form a patch with four times the physical area of a patch extracted at the native resolution of the histological image.

The method can be performed for prediction once the CNN has been trained. The purpose of the training is to assign suitable weight values for the inter-layer connections. For training, ground truth data will be provided which assigns each pixel in the histological image (or set thereof) to one of the tissue classes. The ground truth data will be based on use of an expert clinician to annotate a sufficiently large number of images. Training is carried out by iteratively applying the CNN, where each iteration involves adjusting the weight values based on comparing the ground truth data with the output image patches. In our current implementation, the weights are adjusted during training by gradient descent.

There are various options for setting the tissue classes, but most if not all embodiments will have in common that a distinction will be made in the classes between non-tumorous and tumorous tissue. The non-tumorous tissue classes may include one, two or more classes. The tumorous tissue classes may also include one, two or more classes. For example, in our current implementation we have three tissue classes, one for non-tumorous tissue and two for tumorous tissue, wherein the two tumorous tissue classes are for invasive tumors and in situ tumors.

In some embodiments the CNN is applied to one histological image at a time. In other embodiments the CNN may be applied to a composite histological image formed by combining a set of histological images taken from differently stained, adjacent sections of a region of tissue. In still further embodiments, the CNN may be applied in parallel to each of the images of a set of images taken from differently stained, adjacent sections of a region of tissue.

With the results from the CNN, the method may be extended to include a scoring process based on the pixel classification and the tumors that are defined from that classification with reference to the probability map. For example, the method may further comprise: defining areas in the histological image that correspond to tumors according to the probability map; scoring each tumor according to a scoring algorithm to assign a score to each tumor; and storing the scores, e.g. into a record in a data repository. The scoring thus takes place on the histological image, but is confined to those areas identified by the probability map as containing tumorous tissue.

The results may be displayed on a display to a clinician. Namely, a histological image can be displayed with its associated probability map, e.g. overlaid thereon or alongside each other. The tumor scores may also be displayed in some convenient manner, e.g. with text labels on or pointing to the tumors, or alongside the image.

The convolutional neural network may be a fully convolutional neural network.

A further aspect of the invention relates to a computer program product for identifying tumors in a histological image (or set thereof), the computer program product bearing machine readable instructions for performing the above-described method.

A still further aspect of the invention relates to a computer apparatus for identifying tumors in a histological image (or set thereof)), the apparatus comprising:
an input operable to receive a histological image (or set thereof), e.g. from a stored record, the histological image including a two-dimensional array of pixels;
a processing module configured to:
apply a convolutional neural network to generate an output image with a two-dimensional array of pixels with a mapping to that of the histology image, the output image being generated by assigning one of a plurality of tissue classes to each pixel, wherein the plurality of tissue classes includes at least one class representing non-tumorous tissue and at least one class representing tumorous tissue;
generate a segmentation mask from the output image, in which areas occupied by individual tumors are marked;
compute summary statistics for each tumor; and
apply a filter to the summary statistics of each tumor to edit the segmentation mask by selecting and deselecting tumors according to the filter.

The computer apparatus may further comprise: a post-processing module configured to assemble the output image patches into a probability map for the histological image (or set thereof). Moreover, the computer apparatus may further comprise: an output operable to store the probability map, e.g. into a record in a data repository, so that the probability map is linked to the histological image (or set thereof). The apparatus may still further comprise: a display and a display output operable to transmit the histological image (or set thereof) and the probability map to the display such that the histological image is displayed with the probability map, e.g. overlaid thereon or alongside the probability map.

Another aspect of the invention relates to a system comprising a computer apparatus as specified above in combination with one or more other elements. For example, the system may include an image acquisition apparatus operable to acquire histological images, such as a microscope operable to acquire histological images or sets thereof and to store them to records in the data repository. Such a microscope may be incorporated into a digital scanner. The system may also include a data repository configured to store records of patient data including histological images; and network connections enabling transfer of patient data records or parts thereof between the computer apparatus and the data repository.

In summary, a method, computer apparatus, computer program product and system may be provided for identifying and visualizing tumors in a histological image. A convolutional neural network, CNN, is used to classify pixels in the image according to whether they are determined to relate to non-tumorous tissue, or one or more classes representing tumorous tissue. Segmentation is carried out based on the CNN results to generate a mask in which areas occupied by individual tumors are marked. Summary statistics for each tumor are then computed and supplied to a filter which edits the segmentation mask by filtering out tumors deemed to be insignificant. Optionally, the tumors that pass the filter may be ranked according to the summary statistics, for example in order of clinical relevance or by a sensible order of review for a pathologist. A visualization application can then display the histological image having regard to the segmentation mask, summary statistics and/or ranking.

The histological image may include one or more further two-dimensional array of pixels and thus include a plurality of two-dimensional arrays of pixels, as may be the case, e.g. one for each of a plurality of stains, or one for each of a different depth in the sample (a so-called z-stack) obtained by stepping the focal plane of the microscope through a transparent or semi-transparent sample of finite depth. The output image generated by the CNN will also comprise one or more two-dimensional array of pixels, wherein there is a defined mapping between the (input) histological image(s) and the output image(s), where this may be a one-to-one mapping, a many-to-one mapping or a one-to-many mapping. It will be understood that in at least some embodiments the histological image(s) are digital representations of a two-dimensional image taken of a sectioned tissue sample by a microscope, in particular a light microscope, which may be a conventional optical microscope, a confocal microscope or any other kind of microscope suitable for obtaining histological images of unstained or stained tissue samples. In the case of a set of histological images, these may be of a succession of microscope images taken of adjacent sections (i.e. slices) of a region of tissue, wherein each section may be differently stained. A single histological image may also be a composite computed by merging a plurality of histological images obtained from differently stained, adjacent sections of a region of tissue using a simple overlay or an overlay assisted by warp transformation.

In one embodiment, the CNN may be applied to a computer-automated method for automatically determining tumor margin status after a surgical resection.

According to one aspect of the disclosure, there is provided a method of image processing a histological image to determine margin status of a tumor mass, the method comprising:
receiving a histological image of a tissue sample section obtained from a tumor mass extracted by resection and painted with an ink to highlight its surface, the histological image including a two-dimensional array of pixels;
applying a CNN process using at least one neural network that has been trained to distinguish between tissue classes so as to generate an output image with a two-dimensional array of pixels with a mapping to that of the histology image, the output image being generated by assigning tissue classes to each pixel to distinguish between ink and no-ink as well as tumor and no-tumor;
computing margin status as positive or negative dependent respectively on the presence or absence of tumor-and-ink pixels; and
outputting the margin status.

The positive or negative margin status may be computed at least in part based on whether a count of tumor-and-ink pixels is above or below a threshold number. The positive and negative statuses may be sub-divided. The computation of margin status may subdivide the negative status between close and clear sub-statuses, where close and clear are distinguished by the distance between tumor-and-no-ink pixels and ink-and-no-tumor pixels being below or above a threshold value. The computation of margin status may subdivide the positive status between a plurality of sub-statuses referred to in the art collectively as margin involvement. The margin involvement is said to be focal, minimal/moderate and extensive. The margin involvement can be determined based on the prevalence of tumor-and-ink pixels, where the prevalence may be quantified at least in part based on computing a maximum distance between tumor-and-ink pixels.

We thus propose using an image analysis algorithm that uses deep learning to detect tumor margin status and which is also capable of reporting margin distance and margin involvement. The algorithm can be run unsupervised on a batch of virtual slide images that can then be reviewed by a pathologist. Providing this margin information to the pathologist through this computer-automated method enables an increase in the speed of pathologist workflow and the production of higher quality and more consistent tumor margin reports.

In one group of embodiments, a single convolutional neural network is used to perform the full classification. Namely, the convolutional neural network process comprises applying one neural network that has been trained to distinguish between tissue classes for: tumor and ink, tumor and no ink, no-tumor and ink, and no-tumor and no-ink.

In another group of embodiments separate convolutional neural networks are applied, one for classifying between tumor types and the other for classifying between ink and no-ink, and the results from these two neural networks are logically combined to generate the full set of classes. Namely, the convolutional neural network process comprises separately applying a first neural network trained to distinguish between tissue classes for tumor and no-tumor and output a first output image, and a second neural network trained to distinguish between tissue Classes for ink and no-ink and output a second output image, said output image being generated by combining the first and second output images to assign the tissue classes for: tumor and ink, tumor and no ink, no-tumor and ink, and no-tumor and no-ink.

There may be only one tumor tissue type, or multiple tumor tissue types in the classification scheme. In one embodiment there are separate tumor tissue types for invasive and in situ tumors and one class for non-tumorous tissue, so that a set of six classes is provided bearing in mind that in parallel to the tumor tissue type there is the split between ink and no-ink.

The histological image received by the method for processing may be loaded from a record stored in a virtual slide library or other database, or may be obtained directly after acquisition of the histological image by a digital scanner in which case the method may be carried out by the digital scanner itself or by a computer apparatus, e.g. one connected to the digital scanner, or from another data source.

The method may further comprise, after the assigning step, the step of: assembling the output image into a probability map for the histological image (or set thereof). The method may further comprise, after the assembling step, the step of: storing the probability map linked to the histological image or set thereof, for example in a common record with the probability map constituting metadata for the histological image data.

In our current implementation, in each successive convolution stage, as the dimensions decrease, the depth increases, so that the convolution layers are of ever increasing depth as well as ever decreasing dimensions, and in each successive transpose convolution stage, as the dimensions increase, the depth decreases, so that the deconvolution layers are of ever decreasing depth as well as ever increasing dimensions. The final convolution layer then has a maximum depth as well as minimum dimensions. Instead of the approach of successive depth increases and decreases through respectively the convolution and deconvolution stages, an alternative would be to design a neural network in which every layer except the input layer and the output layer has the same depth.

The method may further comprise: displaying on a display the histological image or set thereof with the probability map, e.g. overlaid thereon or alongside each other.

In certain embodiments, the convolutional neural network has one or more skip connections. Each skip connection takes intermediate results from at least one of the convolution layers of larger dimensions than the final convolution layer and subjects those results to as many transpose convolutions as needed, which may be none, one or more than one, to obtain at least one further recovered layer matched in size to the input image patch. These are then combined with the above-mentioned recovered layer prior to said step of assigning a tissue class to each pixel. A further processing step combines the recovered layer with each of the further recovered layers in order to recompute the probabilities, thereby taking account of the results obtained from the skip connections.

In certain embodiments, a softmax operation is used to generate the probabilities.

The image patches extracted from the histological image(s) may cover the whole area of the image(s). The patches may be non-overlapping image tiles or image tiles that overlap at their margins to aid stitching of the probability map. While each image patch should have a fixed number of pixels in width and height to be matched to the CNN, since the CNN will be designed to accept only a fixed size of pixel array, this does not mean that each image patch must correspond to the same physical area on the histological image, because pixels in the histological image may be combined into a lower resolution patch covering a larger area, e.g. each 2×2 array of neighboring pixels may be combined into one 'super'-pixel to form a patch with four times the physical area of a patch extracted at the native resolution of the histological image.

The method can be performed for prediction once the CNN has been trained. The purpose of the training is to assign suitable weight values for the inter-layer connections. For training, the ground truth data that is used assigns each pixel in the histological image of the training data to one of the tissue classes. The ground truth data will be based on use of an expert clinician to annotate a sufficiently large number of images. Training is carried out by iteratively applying the CNN, where each iteration involves adjusting the weight values based on comparing the ground truth data with the output image patches. In our current implementation, the weights are adjusted during training by gradient descent.

In embodiments that use separate convolutional neural networks, one for classifying between tumor tissue types and the other for classifying between ink and no-ink, supply of training data may be more straightforward, since two separate training data sets can be used, one based solely on tumor segmentation and the other based solely on segmenting an ink boundary. The ink training data can therefore be unspecific to tumor type, or the type of sub-classifications of tumorous tissue type. Moreover, the tumor training data can use any suitable pathology images, not specifically images from resection slides with ink. On the other hand, if the same convolutional neural network is to be used in a 4-way, 6-way or higher even-numbered classification, then the training data sets need to be of images that are of painted resectioned tissue masses that have been suitably expertly analyzed and augmented with ground-truth data.

There are various options for setting the tumor tissue classes, but most if not all embodiments will have in common that a distinction will be made in the classes between non-tumorous and tumorous tissue. The non-tumorous tissue classes may include one, two or more classes. The tumorous tissue classes may also include one, two or more classes. For example, in our current implementation we have three tissue classes, one for non-tumorous tissue and two for tumorous tissue, wherein the two tumorous tissue classes are for invasive tumors and in situ tumors.

In some embodiments the CNN is applied to one histological image at a time. k other embodiments the CNN may be applied to a composite histological image formed by combining a set of histological images taken from differently stained, adjacent sections of a region of tissue. In still further embodiments, the CNN may be applied in parallel to each of the images of a set of images taken from differently stained, adjacent sections of a region of tissue.

The results may be displayed on a display to a clinician. Namely, a histological image can be displayed with its associated probability map, e.g. overlaid thereon or alongside each other. The tumor scores may also be displayed in some convenient manner, e.g. with text labels on or pointing to the tumors, or alongside the image.

The convolutional neural network may be a fully convolutional neural network.

A further aspect of the invention relates to a computer program product for identifying tumors in a histological image or set thereof, the computer program product bearing machine readable instructions for performing the above-described method.

A still further aspect of the invention relates to a computer apparatus for image processing a histological image to determine margin status of a tumor mass, the apparatus comprising:
 an input operable to receive a histological image of a tissue sample section obtained from a tumor mass extracted by resection and painted with an ink to highlight its surface, the histological image including a two-dimensional array of pixels;
 a convolutional neural network processing module comprising at least one neural network that has been trained to distinguish between tissue classes so as to generate an output image with a two-dimensional array of pixels with a mapping to that of the histology image, the output image being generated by assigning tissue classes to each pixel to distinguish between ink and no-ink as well as tumor and no-tumor;
 a margin assessment module operable to compute margin status as positive or negative dependent respectively on the presence or absence of tumor-and-ink pixels in the output image; and
 an output operable to output the margin status.

The output may be connected to a data repository to store the margin status and optionally also the output image into a record. The output image as stored may include a tissue class for each pixel and/or a probability for each pixel, i.e. a probability map. Saving an output image may be useful for constructing visualizations, since for example the histological image can be presented with a tissue class map or probability map overlaid. Whether stored to the record or not, the output may be operable to transmit the histological image and the output image to a display, such that the histological image is displayed with the output image.

Another aspect of the invention relates to a system, such as a clinical network, comprising: a computer apparatus as described above in combination with one or more of the following element: an image acquisition apparatus, such as a microscope, operable to acquire histological images or sets thereof; and a data repository configured to store records of patient data including histological images (or sets thereof). It will be understood that suitable network connections will be provided between ones of these elements enabling data transfer, such as transfer of patient data records or parts thereof between the computer apparatus and the data repository.

It will be understood that in at least some embodiments the histological image(s) are digital representations of a two-dimensional image taken of a sectioned tissue sample by a microscope, in particular a light microscope, which may be a conventional optical microscope, a confocal microscope or any other kind of microscope suitable for obtaining histological images of unstained or stained tissue samples. In the case of a set of histological images, these may be of a succession of microscope images taken of adjacent sections (i.e. slices) of a region of tissue, wherein each section may be differently stained.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Figure 1A:
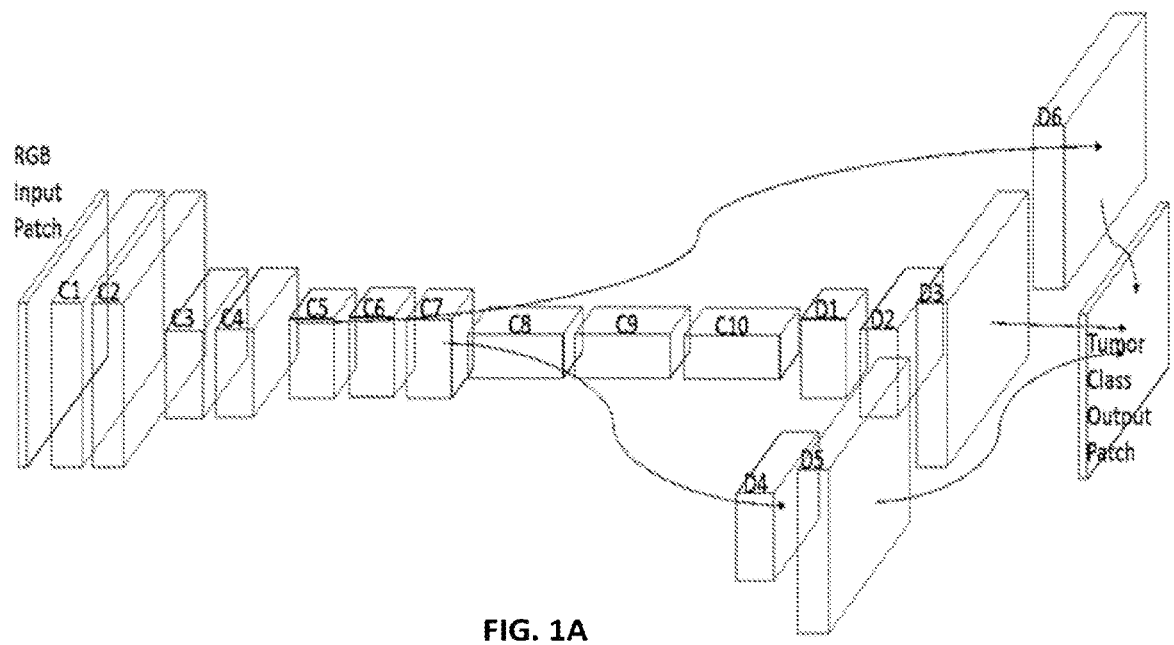
FIG. 1A is a schematic drawing of a neural network architecture used in one embodiment of the invention.

In the following detailed description, for purposes of explanation and not limitation, specific details are set forth in order to provide a better understanding of the present disclosure. It will be apparent to one skilled in the art that the present disclosure may be practiced in other embodiments that depart from these specific details.

Cancer is the second leading cause of death in North American women. Of all types of cancer in women, breast cancer is the most common and the second leading cause of cancer death. Therefore, the accuracy of breast cancer treatment has a great impact on the lifespan and quality of life in the significant percentage of women that will be affected by breast cancer at some point in their lives.

Based on the expression of certain genes, breast cancers can be divided into different molecular subtypes. A commonly used classification scheme is as follows:
1. Luminal A: ER+, PR+, HER2−
2. Luminal B: ER+, PR−, HER2+
3. Triple-Negative Breast Cancer (TNBC): ER−, PR−, HER2−
4. HER2-enriched: HER2+, ER−, PR−
5. Normal-like.

ER stands for estrogen receptor. PR stands for progesterone receptor. HER2 stands for human epidermal growth factor receptor 2.

We describe a computer-automated tumor finding method which detects and outlines invasive and in situ breast cancer cell nuclei automatically. The method is applied to a single input image, such as a WSI, or a set of input images, such as a set of WSIs. Each input image is a digitized, histological image, such as a WSI. In the case of a set of input images, these may be differently stained images of adjacent tissue sections. We use the term stain broadly to include staining with biomarkers as well as staining with conventional contrast-enhancing stains.

Since computer-automated outlining of tumors is much faster than manual outlining, it enables an entire image to be processed, rather than only manually annotating selected extracted tiles from the image. The proposed automatic tumor outlining should thus enable pathologists to compute a positivity (or negativity) percentage over all the tumor cells in the image, which should result in more accurate and reproducible results.

The proposed computer-automated method for tumor finding, outlining and classifying uses a convolutional neural network (CNN) to find each nuclear pixel on the WSI and then to classify each such pixel into one of a non-tumor class and one of a plurality of tumor classes, in our current implementation breast tumor classes.

The neural network in our implementation is similar in design to the VGG-16 architecture available at: <http://www.robots.ox.ac.uk/~vgg,/research/very_deep> and described in Simonyan and Zisserman 2014, the full contents of which are incorporated herein by reference.

The input image is a pathology image stained with any one of several conventional stains as discussed in more detail elsewhere in this document. For the CNN, image patches are extracted of certain pixel dimensions, e.g. 128× 128, 256×256, 512×512 or 1024×1024 pixels. It will be understood that the image patches can be of arbitrary size and need not be square, but that the number of pixels in the rows and columns of a patch conform to 2n, where n is a positive integer, since such numbers will generally be more amenable for direct digital processing by a suitable single CPU (central processing unit), GPU (graphics processing unit) or TPU (tensor processing unit), or arrays thereof.

We note that 'patch' is a term of art used to refer to an image portion taken from a WSI, typically with a square or rectangular shape. In this respect we note that a WSI may contain a billion or more pixels (gigapixel image), so image processing will typically be applied to patches which are of a manageable size (e.g. ca. 500×500 pixels) for processing by a CNN. The WSI will thus be processed on the basis of splitting it into patches, analyzing the patches with the CNN, then reassembling the output (image) patches into a probability map of the same size as the WSI. The probability map can then be overlaid, e.g. semi-transparently, on the WSI, or part thereof, so that both the pathology image and the probability map can be viewed together. In that sense the probability map is used as an overlay image on the pathology image. The patches analyzed by the CNN may be of all the same magnification, or may have a mixture of different magnifications, e.g. 5×, 20×, 50× etc. and so correspond to different sized physical areas of the sample tissue. By different magnifications, these may correspond to the physical magnifications with which the WSI was acquired, or effective magnifications obtained from digitally downscaling a higher magnification (i.e. higher resolution) physical image.

FIG. 1A is a schematic drawing of our neural network architecture. Layers C1, C2 . . . C10 are convolutional layers. Layers D1, D2, D3, D4, D5 and D6 are transpose convolution (i.e. deconvolutional) layers. The lines interconnecting certain layers indicate skip connections between convolutional, C, layers and deconvolutional, D, layers. The skip connections allow local features from larger dimension, shallower depth layers (where "larger" and "shallow" mean a convolutional layer of lower index) to be combined with the global features from the last (i.e. smallest, deepest) convolutional layer. These skip connections provide for more accurate outlines. Maxpool layers, each of which is used to reduce the width and height of the patch by a factor of 2, are present after layers C2, C4 and C7, but are not directly shown in the schematic, although they are shown by implication through the consequential reducing size of the patch. In some implementations of our neural network the maxpool layers are replaced with 1×1 convolutions resulting in a fully convolutional network.

The convolutional part of the neural network has the following layers in sequence: input layer (RGB input image patch); two convolutional layers, C1, C2; a first maxpool layer (not shown); two convolutional layers C3, C4; a second maxpool layer (not shown); three convolutional layers, C5, C6, C7, and a third maxpool layer (not shown). The output from the second and third maxpool layers is connected directly to deconvolutional layers using skip connections in addition to the normal connections to layers C5 and C8, respectively.

The final convolutional layer, C10, the output from the second maxpool layer (i.e. the one after layer C4) and the output from the third maxpool layer (i.e. the one after layer C7), are then each connected to separate sequences of "deconvolution layers" which upscale them back to the same size as the input (image) patch, i.e. convert the convolutional feature map to a feature map which has the same width and height as the input image patch and a number of channels (i.e. number of feature maps) equal to the number of tissue classes to be detected, i.e. a non-tumorous type and one or more tumor types. For the second maxpool layer, we see a direct link to the layer D6 since only one stage of deconvolution is needed. For the third maxpool layer, two stages of deconvolution are needed, via intermediate deconvolution layer D4, to reach layer D5. For the deepest convolutional layer C10, three stages of deconvolution are needed, via D1 and D2 to layer D3. The result is three arrays D3, D5, D6 of equal size to the input patch.

A simplified, albeit probably less-well performing, version of what is illustrated in FIG. 1A could omit the skip connections, in which case layers D4, D5 and D6 would not be present and the output patch would be computed solely from layer D3.

Figure 1B:
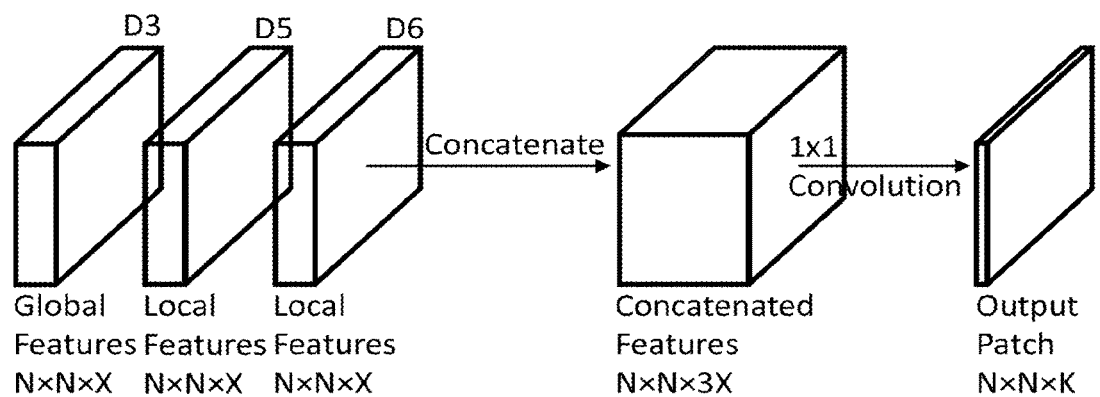
FIG. 1B shows how within the neural network architecture of FIG. 1A global and local feature maps are combined to generate a feature map that predicts an individual class for each pixel in an input image patch.

FIG. 1B shows in more detail how the final steps in the neural network architecture of FIG. 1A are carried out. Namely, global feature map layer D3 and local feature map layers D5, D6 are combined to generate a feature map that predicts an individual class for each pixel of the input image patch. Specifically, FIG. 1B shows how the final three transpose convolution layers D3, D5, D6 are processed to the tumor class output patch.

We now discuss how the above-described approach differs from a known CNN used currently in digital pathology. This known CNN assigns one class selected from multiple available classes to each image patch. Examples of such type of CNN are in the papers by Wang et al 2016, Liu et al 2017, Cruz-Roa et al 2017 and Vandenberghe et al 2017. However, what we have just described is that, within a given image patch, one class selected from multiple available classes is assigned to each and every pixel. Therefore, instead of generating a single class label for each image patch, our neural network outputs a class label for each individual pixel of a given patch. Our output patch has a one-to-one pixel-to-pixel correspondence with the input patch such that each pixel in the output patch has assigned to it one of the multiple available classes (non-tumor, tumor 1, tumor 2, tumor 3 etc.).

In such known CNNs, to assign a single class to each patch, a series of convolutional layers is employed followed by one or several fully connected layers, followed by an output vector which has as many values as there are classes to detect. The predicted class is determined by the location of the maximum value in the output vector.

A trained CNN will take, as input, pixels from a digital slide image and return a vector of probabilities for each pixel (Goodfellow, Bengio, and Courville 2016). The vector is of length N where N is the number of classes the CNN has been trained to detect. For example, if a CNN has been trained to distinguish between three classes, invasive tumor, in situ tumor and non-tumor, the vector v will be of length 3. Each coordinate in the vector indicates the probability that the pixel belongs to a specific class. So v[0] may indicate the probability that the pixel belongs to the invasive tumor class, v[1] the probability it belongs to the in situ class and v[2] the probability it belongs to the non-tumor class. The class of each pixel is determined from the probability vector. A simple method of assigning a pixel to a class is to assign it to the class for which it has the highest probability.

To predict the class of individual pixels, our CNN uses a different architecture following the convolutional layers. Instead of a series of fully connected layers, we follow the convolutional layers with a series of transpose convolutional layers. The fully connected layers are removed from this architecture. Each transpose layer doubles the width and height of the feature maps while at the same time halving the number of channels. In this manner, the feature maps are upscaled back to the size of the input patch.

In addition, to improve the prediction, we use skip connections as described in Long et al 2015, the full contents of which is incorporated herein by reference.

The skip connections use shallower features to improve the coarse predictions made by upscaling from the final convolutional layer C10. The local features from the skip connections contained in layers D5 and D6 of FIG. 1A are concatenated with the features generated by upscaling the global features contained in layer D3 of FIG. 1A from the final convolutional layer. The global and local feature layers D3, D5 and D6 are then concatenated into a combined layer as shown in FIG. 1B.

From the concatenated layer of FIG. 1B (or alternatively directly from the final deconvolutional layer D3 in the case that skip connections are not used), the number of channels is reduced to match the number of classes by a 1×1 convolution of the combined layer. A softmax operation on this classification layer then converts the values in the combined layer into probabilities. The output patch layer has size N×N×K, where N is the width and height in pixels of the input patches and K is the number of classes that are being detected. Therefore, for any pixel P in the image patch there is an output vector V of size K. A unique class can then be assigned to each pixel P by the location of the maximum value in its corresponding vector V.

The CNN thus labels each pixel as non-cancerous or belonging to one or more of several different cancer (tumor) types. The cancer of particular interest is breast cancer, but the method is also applicable to histological images of other cancers, such as cancer of the bladder, colon, rectum, kidney, blood (leukemia), endometrium, lung, liver, skin, pancreas, prostate, brain, spine and thyroid.

Our specific neural network implementation is configured to operate on input images having certain fixed pixel dimensions. Therefore, as a preprocessing step, both for training and prediction, patches are extracted from the WSI which have the desired pixel dimensions, e.g. N×N×n pixels, where n=3 in the case that each physical location has three pixels associated with three primary colors—typically RGB, when the WSI is a color image acquired by a conventional visible light microscope. (As mentioned further below 'n' may be 3 times the number of composited WSIs in the case the two or more color WSIs are combined.) Moreover 'n' would have a value of one in the case of a single monochrome WSI. To make training faster the input patches are also centered and normalized at this stage.

Our preferred approach is to process the entire WSI, or at least the entire area of the WSI which contains tissue, so the patches in our case are tiles that cover at least the entire tissue area of the WSI. The tiles may be abutting without overlap, or have overlapping edge margin regions of for example 1, 2, 3, 4, 5, 6, 7, 8, 9 or 10 pixels wide so that the output patches of the CNN can be stitched together taking account of any discrepancies. Our approach can however, if desired, also be applied to a random sample of patches over the WSI which are of the same or different magnification, as in the prior art, or as might be carried out by a pathologist.

Our neural network is similar in design to the VGG-16 architecture of Simonyan and Zisserman 2014. It uses very small 3×3 kernels in all convolutional filters. Max pooling is performed with a small 2×2 window and stride of 2. In contrast to the VGG-16 architecture, which has a series of fully connected layers after the convolutional layers, we follow the convolution layers with a sequence of "deconvolutions" (more accurately transpose convolutions) to generate segmentation masks. This type of upsampling for semantic segmentation has previously been used for natural image processing by Long et al 2015, the full contents of which are incorporated herein by reference.

Each deconvolutional layer enlarges the input feature map by a factor of two in the width and height dimensions. This counteracts the shrinking effect of the maxpool layers and results in class feature maps of the same size as the input images. The output from each convolution and deconvolutional layer is transformed by a non-linear activation layer. At present, the non-linear activation layers use the rectifier function ReLU (x)=max (0, x)ReLU(x)=max(0,x). Different activation functions may be used, such as ReLU, leaky ReLU, eLU, etc. as desired.

The proposed method can be applied without modification to any desired number of tissue classes. The constraint is merely the availability of suitable training data which has been classified in the manner that it is desired to replicate in the neural network. Examples of further breast pathologies are invasive lobular carcinoma or invasive ductal carcinoma, i.e. the single invasive tumor class of the previous example can be replaced with multiple invasive tumor classes. The accuracy of the neural network is mostly dictated by the number of images available for each class, how similar the classes are, and how deep the neural network can be made before running into memory restrictions. In general, high numbers of images per class, deeper networks and dissimilar classes lead to higher network accuracy.

A softmax regression layer (i.e. multinomial logistic regression layer) is applied to each of the channel patches to convert the values in the feature map to probabilities.

After this final transformation by the softmax regression, a value at location location (x, y) in a channel C in the final feature map contains the probability, P(x, y), that the pixel at location location (x, y) in the input image patch belongs to the tumor type detected by channel C.

It will be appreciated that the number of convolution and deconvolution layers can be increased or decreased as desired and subject memory limitations of the hardware running the neural network.

We train the neural network using mini-batch gradient descent. The learning rate is decreased from an initial rate of 0.1 using exponential decay. We prevent neural network overfitting by using the "dropout" procedure described by Srivastava et al 2014 [2017], the full contents of which are incorporated herein by reference. Training the network may be done on a GPU, CPU or a FPGA using any one of several available deep learning frameworks. For our current implementation, we are using Google Tensor-flow, but the same neural network could have been implemented in another deep learning framework such as Microsoft CNTK.

The neural network outputs probability maps of size N×N×K, where N is the width and height in pixels of the input patches and K is the number of classes that are being detected. These output patches are stitched back together into a probability map of size W×H×K, where W and H are the width and height of the original WSI before being split into patches.

The probability maps can then be collapsed to a W×H label image by recording the class index with maximum probability at each location (x, y) in the label image.

In its current implementation, our neural network assigns every pixel to one of three classes: non-tumor, invasive tumor and in situ tumor.

When multiple tumor classes are used, the output image can be post-processed into a simpler binary classification of non-tumor and tumor, i.e. the multiple tumor classes are combined. The binary classification may be used as an option when creating images from the base data, while the multi-class tumor classification is retained in the saved data.

While the above description of a particular implementation for our invention has concentrated on a specific approach using a CNN, it will be understood that our approach can be implemented in a wide variety of different types of convolutional neural network. In general, any neural network that uses convolution to detect increasingly complex features and subsequently uses transpose convolutions ("deconvolutions") to upscale the feature maps back to the width and height of the input image should be suitable.

Example 1

FIGS. 2A-2D are color images in operation and show the difference between patch-level predictions such as those generated by Google's CNN solution for the Camelyon competition (Liu et al. 2017) and the pixel-level predictions for tumor class generated by the presently described CNN.

Figure 2A:
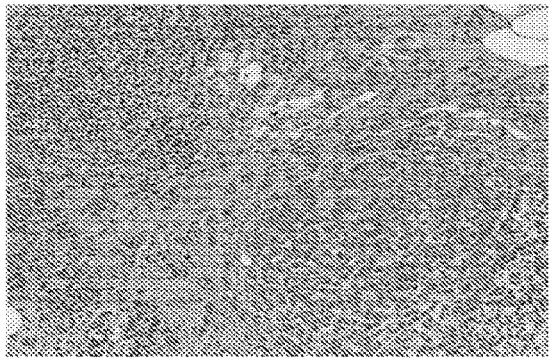
FIG. 2A is a drawing showing a raw histology patch image that in operation is a color image.
Figure 2B:
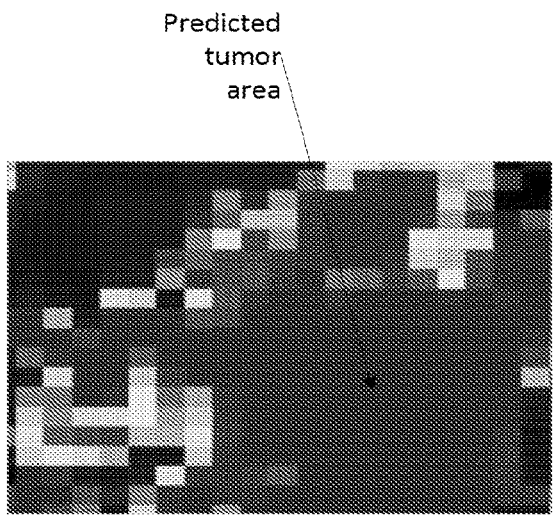
FIG. 2B is a drawing showing the CNN prediction of FIG. 2A that in operation is a color image. The CNN prediction illustrates the predicted tumor area, which is in dark red in the color image.
Figure 2C:
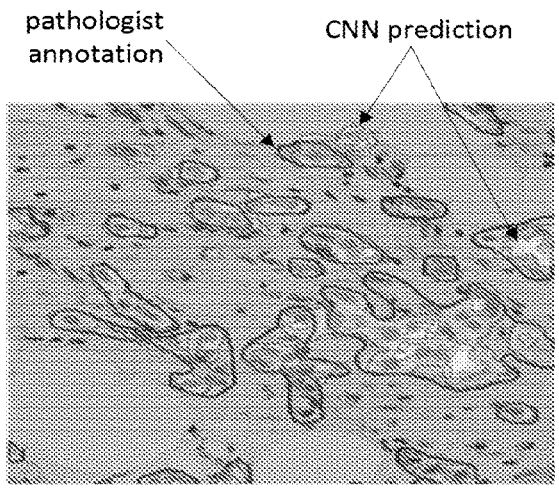
FIG. 2C is a drawing showing the raw histology image that in operation is a color image. The marked up raw histology image illustrates pathologist hand-annotations (red) and CNN predictions (pink and yellow).
Figure 2D:
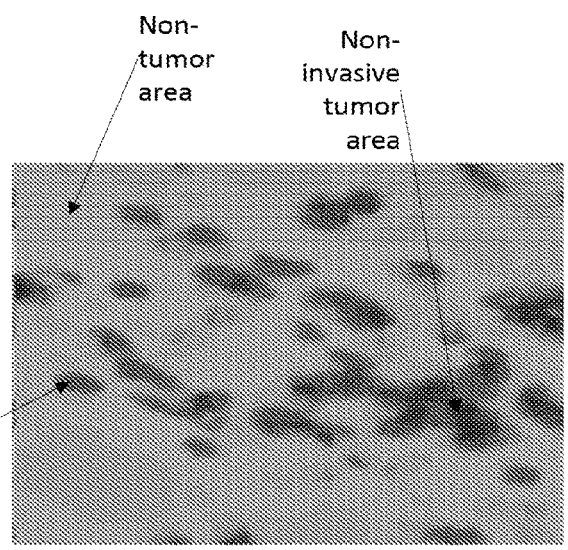
FIG. 2D is a drawing showing the CNN prediction that in operation is a color image. The CNN prediction image illustrates non-tumor area (green), invasive tumor area (red, which corresponds to pink in FIG. 2C), and non-invasive tumor (blue, which corresponds to yellow in FIG. 2C).
Figure 7:
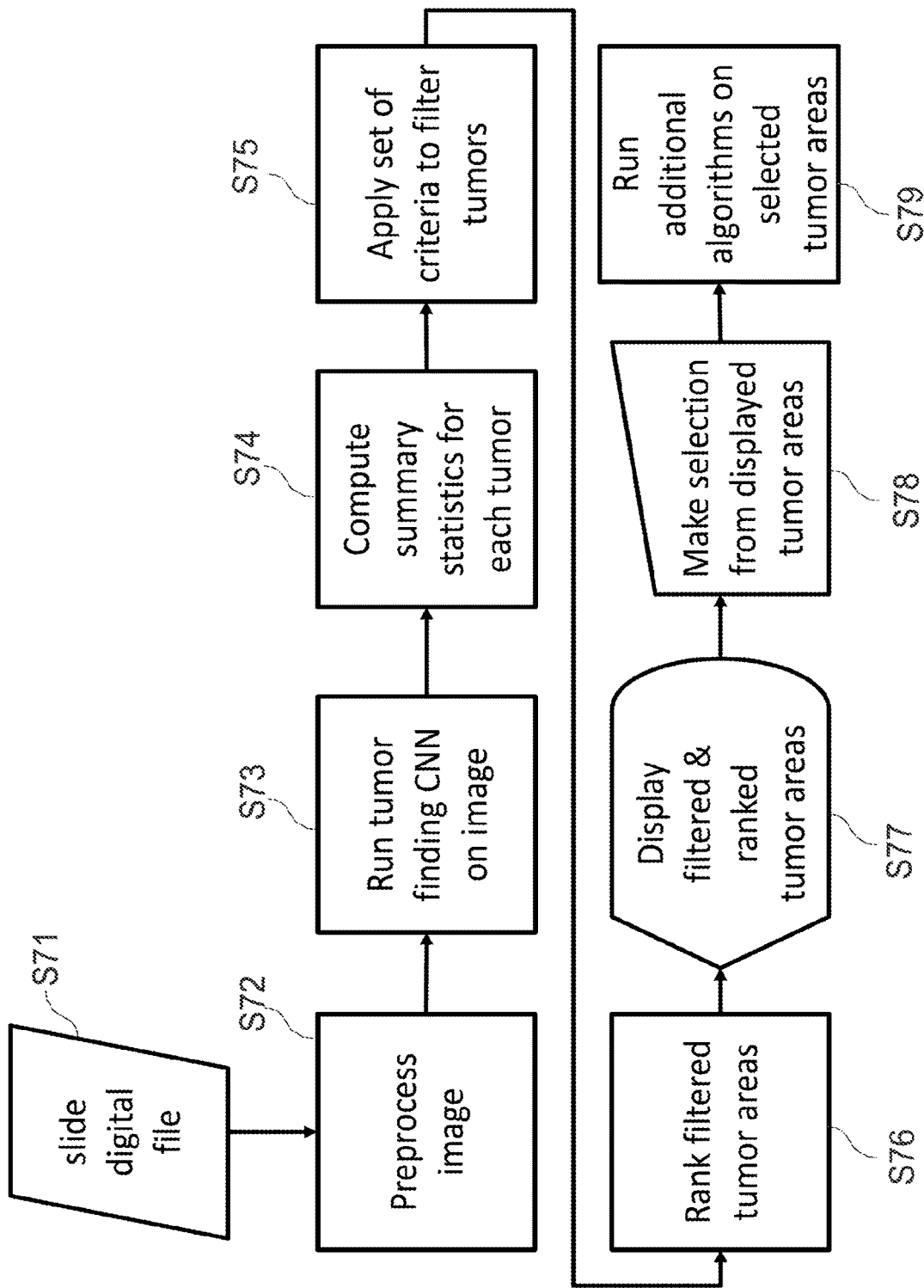
FIG. 7 is a flow diagram of a method according to an embodiment of the present disclosure.

FIGS. 2A and 2B are copied from FIG. 7 of Liu et al 2017, whereas FIG. 2C and FIG. 2D are comparable tiles for an example according to the presently described CNN as applied to classify by tumor tissue class (not including ink/no-ink).

FIG. 2A is a patch from an H&E-stained WSI in which the cluster of larger, dark purple cells in the bottom right quadrant is a tumor, while the smaller dark purple cells are lymphocytes.

FIG. 2B is a tumor probability heatmap generated by the CNN of Liu et al 2017 which the authors state accurately identifies the tumor cells, while ignoring the connective tissue and lymphocytes.

FIG. 2C is a raw image patch from an example WSI to which the CNN method embodying the invention is applied. As well as the raw image, FIG. 2C shows outlines drawn manually by a pathologist (solid red perimeter lines). In addition, with reference to FIG. 2D, FIG. 2C also shows results from the presently described CNN method (first areas shaded pink with pink perimeter lines correspond to a first tumor type, i.e. the tumor type shown red in FIG. 2D; second areas shaded yellow with pink perimeter lines correspond to a second tumor type, i.e. the tumor type shaded blue in FIG. 2D).

FIG. 2D is a tumor probability heatmap generated by our CNN. It can be seen how our approach of pixel-level prediction produces areas with smooth perimeter outlines. For our heatmap, different (arbitrarily chosen) colors indicate different classes, namely green for non-tumor, red for a first tumor type and blue for a second tumor type.

Example 2

Figure 3A:
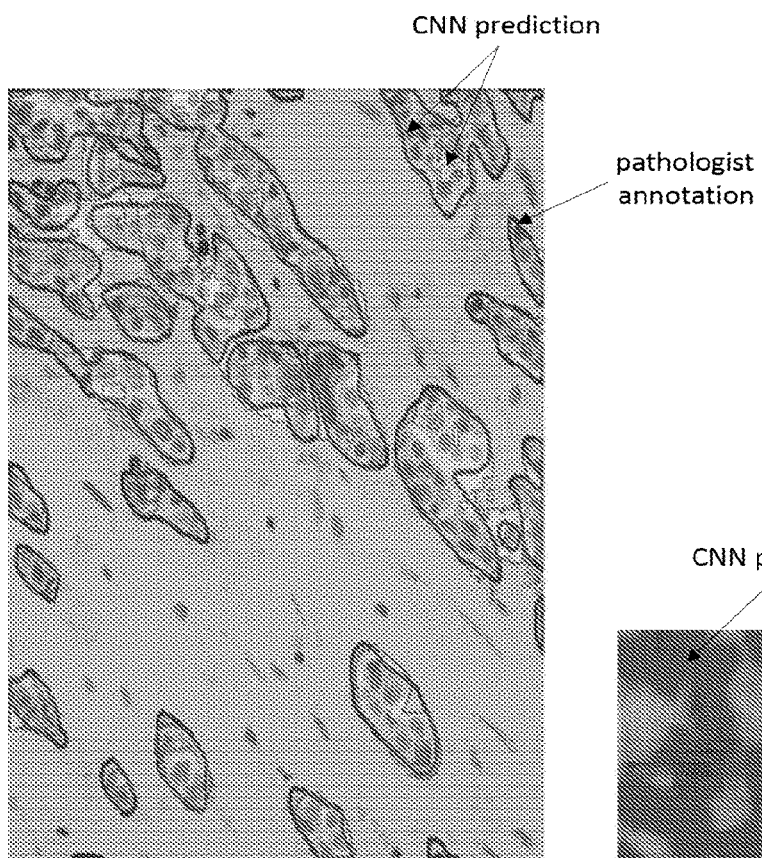
FIG. 3A is a drawing showing an example of the input RGB image patch that in operation is a color image. The image patch shows the pathologist's manual outlining of invasive tumors (red) and additionally shows overlays of the neural network's predictions (pink and yellow).
Figure 3B:
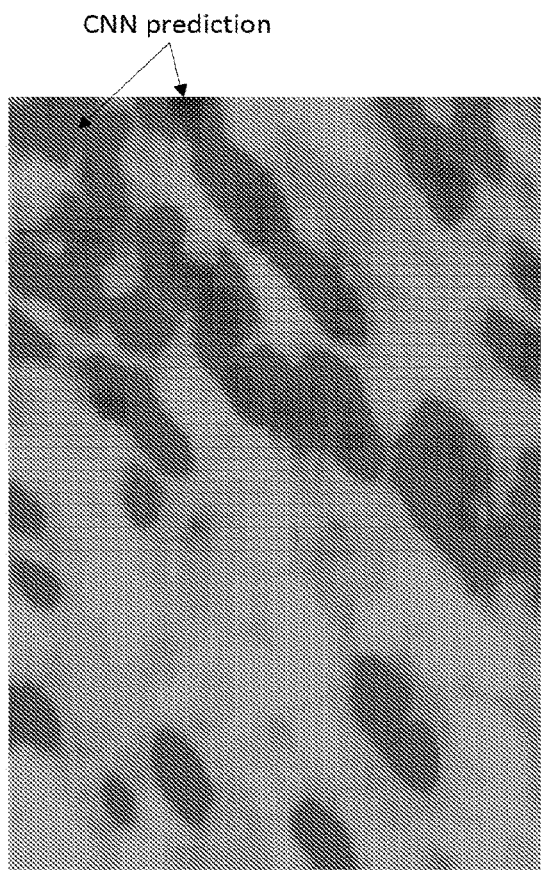
FIG. 3B is a drawing showing the final output tumor probability heat map that in operation is a color image. The heat map shows overlays of the neural network's predictions (in reddish-brown and blue respectively).

FIGS. 3A-3B are color images in operation and show an example of the input RGB image patch (FIG. 3A) and the final output tumor probability heat map (FIG. 3B).

FIG. 3A additionally shows the pathologist's manual outlining of invasive tumors (red outlines) and in addition overlays of our neural networks predictions (shaded pink and yellow areas) as separately shown in FIG. 3B.

FIG. 3B is a tumor probability heatmap generated by our CNN. For our heatmap, different (arbitrarily chosen) colors indicate different classes, namely green for non-tumor, reddish-brown for invasive tumor (shown pink in FIG. 3A), and blue for in situ tumor (shown yellow in FIG. 3A). Once again, it can be seen how our approach of pixel-level prediction produces areas with smooth perimeter outlines. Moreover, it can be seen how the CNN predictions are compatible with the pathologist's manual marking. In addition, the CNN provides a further distinction between invasive and non-invasive (in situ) tissue which was not carried out by the pathologist, and is inherently part our multi-channel CNN design which can be programmed to and trained for classifying tissue into any number of different types as desired and clinically relevant.

Acquisition & Image Processing

The starting point of the method is that a tissue sample has been sectioned, i.e. sliced, and adjacent sections have been stained with different stains. The adjacent sections will have very similar tissue structure, since the sections are thin, but will not be identical, since they are of different layers.

For example, there could be 5 adjacent sections, each with a different stain, such as ER, PR, p53, HER2, H&E and Ki-67. A microscope image is then acquired of each section. Although the adjacent sections will have very similar tissue shapes, the stains will highlight different features, e.g. nucleus, cytoplasm, all features by general contrast enhancement etc.

The different images are then aligned, warped or otherwise pre-processed to map the coordinates of any given feature on one image to the same feature on the other images. The mapping will take care of any differences between the images caused by factors such as slightly different magnifications, orientation differences owing to differences in slide alignment in the microscope or in mounting the tissue slice on the slide, and so forth.

It is noted that with a coordinate mapping between different WSIs of a set comprising differently stained adjacent sections, the WSIs can be merged into a single composite WSI from which composite patches may be extracted for processing by the CNN, where such composite patches would have dimensions N×N×3m, where 'm' is the number of composited WSIs forming the set.

Some standard processing of the images is then carried out. These image processing steps may be carried out on the WSI level or at the level of individual image patches. The images may be converted from color to grayscale if the CNN is configured to operate on monochrome rather than color images. The images may be modified by applying a contrast enhancement filter. Some segmentation may then be performed to identify common tissue areas in the set of images or simply to reject background that does not relate to tissue. Segmentation may involve any or all of the following image processing techniques:

1. Variance based analysis to identify the seed tissue areas
2. Adaptive thresholding
3. Morphological operations (e.g. blob analysis)
4. Contour identification
5. Contour merging based on proximity heuristic rules
6. Calculation of invariant image moments
7 Edge extraction (e.g. Sobel edge detection)
8. Curvature flow filtering
9. Histogram matching to eliminate intensity variations between serial sections
10. Multi-resolution rigid/affine image registration (gradient descent optimizer)
11. Non-rigid deformation/transformation
12. Superpixel clustering It will also be understood that image processing steps of the above kind can be carried on the WSIs or on individual patches after patch extraction. In some cases, it may be useful to carry out the same type of image processing both before and after patch extraction, i.e. as CNN pre-processing and CNN post-processing respectively. That is, some image processing may be done on the WSI before patch extraction and other image processing may be done on a patch after its extraction from the WSI.

These image processing steps are described by way of example and should not be interpreted as being in any way limitative on the scope of the invention. For example, the CNN could work directly with color images if sufficient processing power is available.

Training & Prediction

Figure 4:
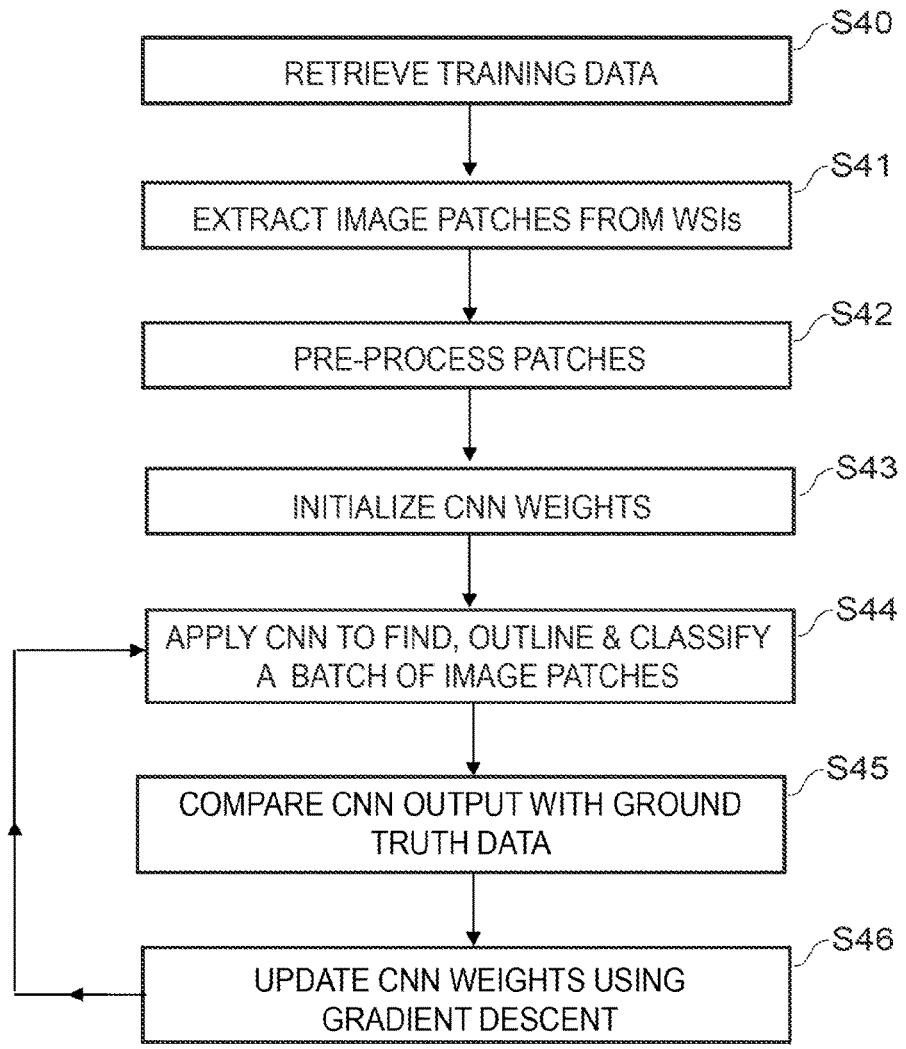
FIG. 4 is a flow diagram showing the steps involved in training the CNN.

FIG. 4 is a flow diagram showing the steps involved in training the CNN.

In Step S40, training data is retrieved containing WSIs for processing which have been annotated by a clinician to find, outline and classify tumors. The clinician's annotations represent the ground truth data.

In Step S41, the WSIs are broken down into image patches, which are the input image patches for the CNN. That is, image patches are extracted from the WSI.

In Step S42, the image patches are pre-processed as described above. (Alternatively, or in addition, the WSIs could be pre-processed as described above prior to Step S41.)

In Step S43, initial values are set for the CNN weights, i.e. the weights between layers.

In Step S44, each of a batch of input image patches is input into the CNN and processed to find, outline and classify the patches on a pixel-by-pixel basis as described further above with reference to FIGS. 1A and 1B. The term outline here is not necessarily strictly technically the right term to use, since our method identifies each tumor (or tumor type) pixel, so it is perhaps more accurate to say that the CNN determines tumor areas for each tumor type.

In Step S45, the CNN output image patches are compared with the ground truth data. This may be done on a per-patch basis. Alternatively, if patches have been extracted that cover the entire WSI, then this may be done at the WSI level, or in sub-areas of the WSI made up of a contiguous batch of patches, e.g. one quadrant of the WSI. In such variants, the output image patches can be reassembled into a probability map for the entire WSI, or contiguous portion thereof, and the probability map can be compared with the ground truth data both by the computer and also by a user visually if the probability map is presented on the display as a semi-transparent overlay to the WSI, for example.

In Step S46, the CNN then learns from this comparison and updated the CNN weights, e.g. using a gradient descent approach. The learning is thus fed back into repeated processing of the training data as indicated in FIG. 4 by the return loop in the process flow, so that the CNN weights can be optimized.

After training, the CNN can be applied to WSIs independently of any ground truth data, i.e. in live use for prediction.

Figure 5:
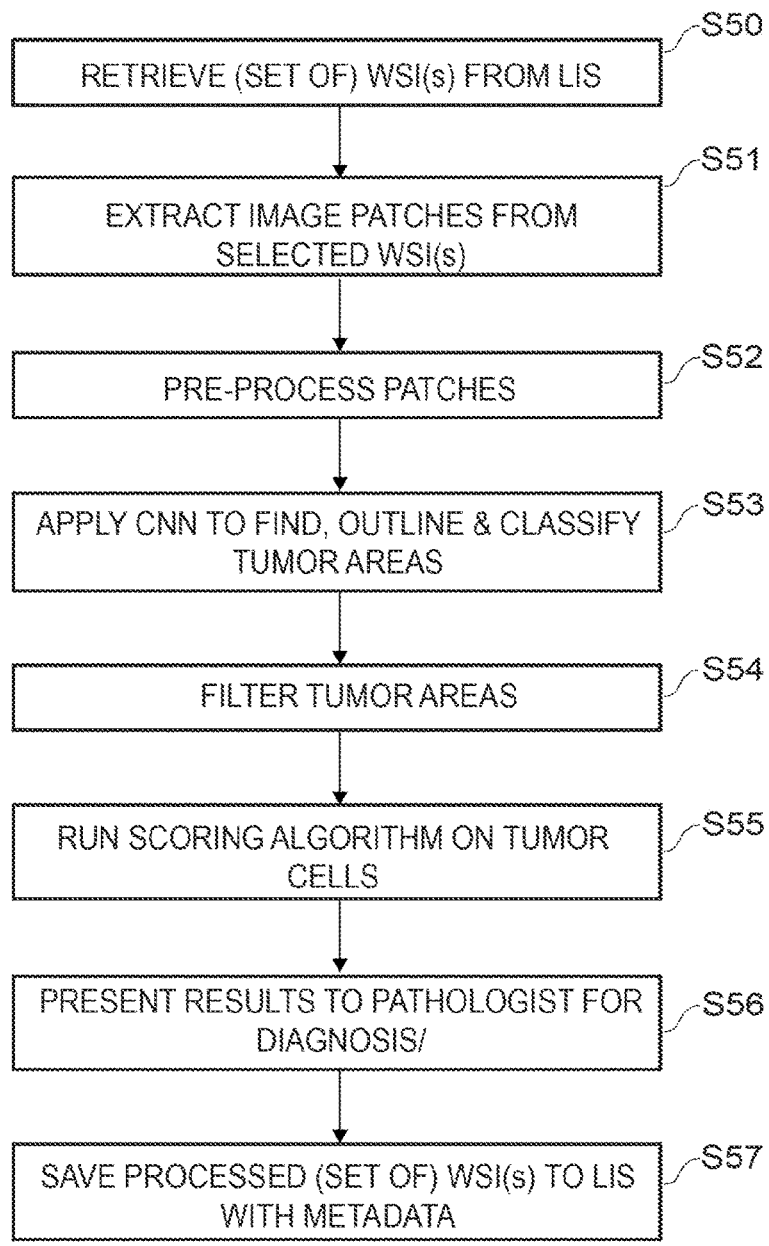
FIG. 5 is a flow diagram showing the steps involved in prediction using the CNN.

FIG. 5 is a flow diagram showing the steps involved in prediction using the CNN.

In Step S50, one or more WSIs are retrieved for processing, e.g. from a laboratory information system (LIS) or other histological data repository. The WSIs are pre-processed, for example as described above.

In Step S51, image patches are extracted from the or each WSI. The patches may cover the entire WSI or may be a random or non-random selection.

In Step S52, the image patches are pre-processed, for example as described above.

In Step S53, each of a batch of input image patches is input into the CNN and processed to find, outline and classify the patches on a pixel-by-pixel basis as described further above with reference to FIGS. 1A and 1B. The output patches can then be reassembled as a probability map for the WSI from which the input image patches were extracted. The probability map can be compared with the WSI both by the computer apparatus in digital processing and also by a user visually, if the probability map is presented on the display as a semi-transparent overlay on the WSI or alongside the WSI, for example.

In Step S54, the tumor areas are filtered excluding tumors that are likely to be false positives, for example areas that are too small or areas that may be edge artifacts.

In Step S55, a scoring algorithm is run. The scoring is cell specific and the score may be aggregated for each tumor, and/or further aggregated for the WSI (or sub-area of the WSI).

In Step S56, the results are presented to a pathologist or other relevantly skilled clinician for diagnosis, e.g. by display of the annotated WSI on a suitable high-resolution monitor.

In Step S57, the results of the CNN, i.e. the probability map data and optionally also metadata relating to the CNN parameters together with any additional diagnostic information added by the pathologist, are saved in a way that is linked to the patient data file containing the WSI, or set of WSIs, that have been processed by the CNN. The patient data file in the LIS or other histological data repository is thus supplemented with the CNN results.

Margin Assessment

Figure 6:
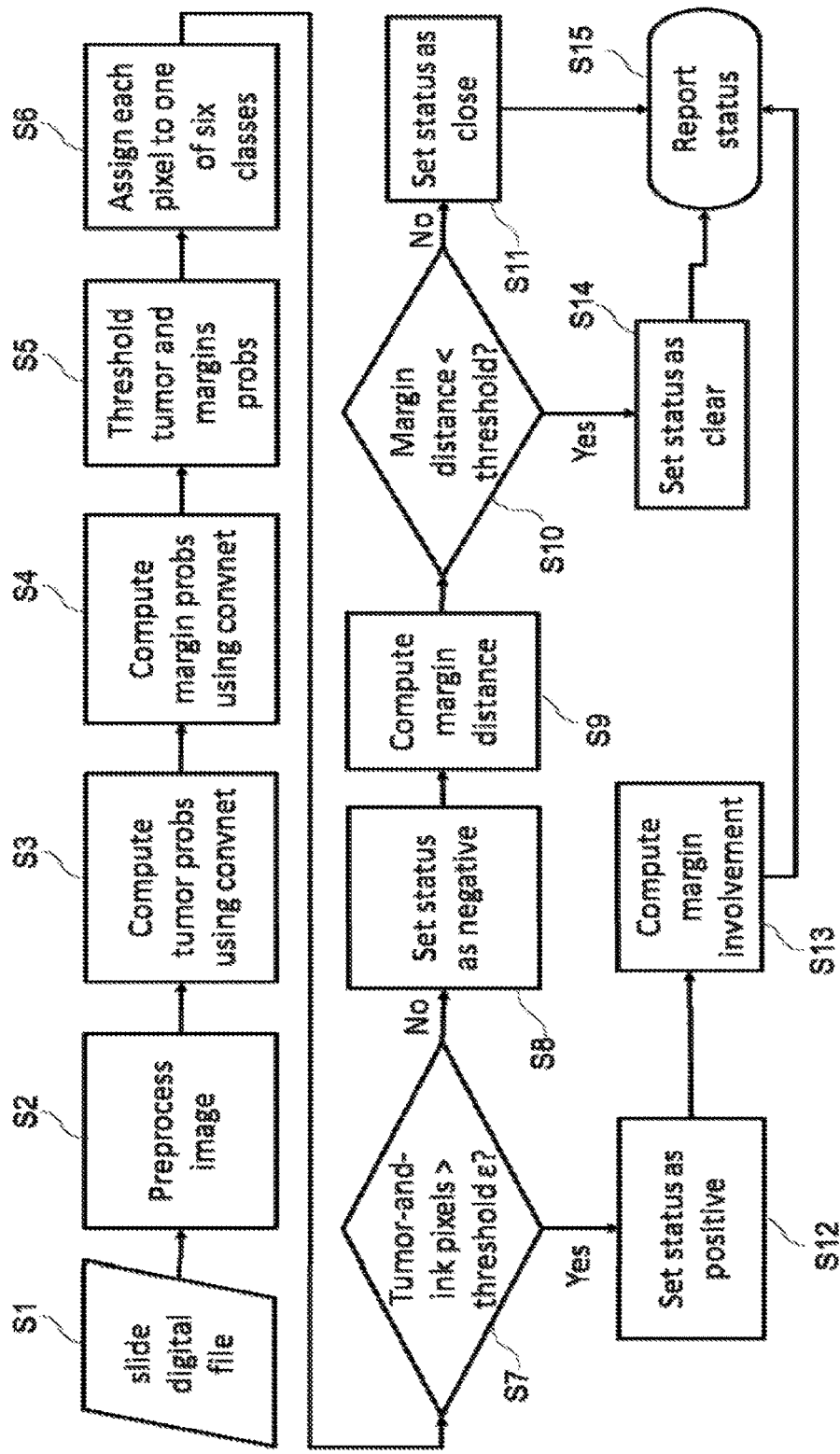
FIG. 6 is a flow diagram showing the steps involved in using the trained CNN to assess margins.

FIG. 6 is a flow diagram showing the steps involved in prediction using the CNN.

In Step S1, one or more WSIs of inked and stained tissue samples are retrieved for processing, e.g. using a laboratory information system (LIS) to retrieve the data from a virtual slide library or other histological data repository.

In Step S2, the WSIs are pre-processed, for example as described above.

In Step S3, a first CNN is applied to perform the 3-way tissue type classification (non-tumor, invasive tumor, in situ tumor). Image patches are extracted from the one or more WSI. The patches may cover the entire WSI or may be a random or non-random selection. The image patches may be pre-processed, for example as described above. Each of a batch of input image patches is input into the CNN and processed to classify the patches on a pixel-by-pixel basis as described further above with reference to FIGS. 1A and 1B. The output patches are reassembled as a probability map of the tumor locations.

In Step S4, a second CNN is applied to perform the binary classification to recognize ink pixels (ink, no-ink). A probability map is generated as described for Step S3, where this time the probability map identifies the ink locations, i.e. the boundary of the tissue mass.

In Step S5, some post-processing of the two probability maps is performed to filter the probability values according to simple thresholding or some more complex numerical processing. For example, segmentation may be applied to the probability values to identify an ink boundary and then adjust the probability values of pixels of ink categories accordingly. Post-processing may also use segmentation to exclude tumor areas that are likely to be false positives, for example areas that are too small or areas that may be edge artifacts. If desired the two probability maps output from Steps S3 and S4 could be merged or combined into a single probability map and the post-processing applied to the merged probability map.

As described further above, Steps S3 and S4 are effectively merged in other embodiments in which a single CNN performs a 6-way classification and generates a single probability map, in which case the post-processing of Step S5 would be performed on the single probability map. (It is also noted that the probability maps may also be used to generate visualizations in a viewing application, e.g. as overlays for the histological image, which could be presented to a pathologist together with the margin assessment data output from the process flow of FIG. 6.)

In Step S6, a mask is created by assigning each pixel to one of the six classes. (It is also noted that the mask may also be used to generate visualizations in a viewing application, e.g. as one or more overlays for the histological image, such as an ink boundary overlay or a tumor pixel overlay. These overlays could be presented to a pathologist together with the margin assessment data output from the process flow of FIG. 6.)

In Step S7, it is determined whether there is more than a threshold number c of pixels in the tumor-and-ink classes. If 'no', the margin status is set as 'negative' in Step S8 and the process flow proceeds to compute margin distance, whereas if 'yes' the margin status is set as 'positive' in Step S12 and the process flow proceeds to compute margin involvement, i.e. the extent to which tumorous tissue has encroached on the boundary of the tissue mass excised by the resection surgery. The threshold text could apply a single threshold to the sum of pixels in all tumor-and-ink classes, or separate thresholds for separate sums of each tumor-and-ink class. For example, in the latter case, if either the "invasive tumor and ink" or the "in situ tumor on ink" classes are detected at a level higher than a respective threshold values (which may be the same or different), the threshold test result is 'yes' and the margin status is "positive", whereas if the level is equal to or lower in both threshold comparisons, then the test result is no and the margin status is "negative". The threshold(s) can be set to empirically defined value(s) or any other suitable value(s).

Following the negative branch, in Step S9, margin distance is computed and, in Step S10, tested against a suitable threshold. If pixels in the tumor-on-ink classes are detected at a level below the threshold c then there is a margin and thus the margin status must be either "clear" or "close" depending on the margin distance. In Step S11, if margin distance is below the threshold, then the status is set to negative/close. In Step S14, if margin distance is below the threshold, then the status is set to negative/clear. We define margin distance as the closest distance between tumor tissue and the inked surface. One can define the set S1 as containing the coordinates $(x_t, y_t) \in R^2$ of all the tumor pixels and the set S2 as containing the coordinates $(x_m, y_m) \in R^2$ of all the margin pixels. Therefore, the problem of computing the margin distance is the problem of computing the minimum distance between two sets of planar points. It has been shown that this measure can be computed in $O(n \log n)$ time and can therefore be computed quickly for even large sets of points (Toussaint and Bhattacharya 1983). If the margin distance Dm is below a specified threshold θ, as may be set by the user, the margin status is returned as "close". If $Dm \geq \theta$, the margin status is returned as "clear". Of course, the actual computed margin distance may be output. This may be a simple number representing the smallest distance, or a more sophisticated output providing additional data such as separate distances for smallest and largest margin distances, statistical values such as average margin distance and its probability distribution, e.g. in terms of standard deviations.

Following the positive branch, in Step S13 margin involvement is computed. Since pixels in the tumor-and-ink classes have been detected at a level at or above the, or one of the, thresholds c, then there is no tumor-free margin, i.e. there is a positive margin. For positive margins, the margin involvement may be computed as the total length of tumor cells on the ink surface. This is equivalent to finding the maximum distance between two pixels belonging to each tumor and summing the result. Since this is problem is equivalent to the minimum distance problem it also can be solved in $O(n \log n)$ time (Vaidya 1989). The current College of American Pathologists guidelines only ask for approximate extent to be reported. One scheme for classifying the extent of margin involvement based on the total lengths is as follows:

Unifocal: one focal area of carcinoma at the margin with a maximum distance less than a threshold of, for example, <4 mm Multifocal: two or more foci of carcinoma at the margin, with a sum of their maximum distances being less than the unifocal threshold Minimal/moderate: as for unifocal or multifocal but with the sum of the maximum distances being less than a second threshold that is greater than the threshold employed for the unifocal and multifocal classifications, for example <5 mm.

Extensive: carcinoma present at the margin over a broad front (sum of maximum distances >5 mm)

If desired, unifocal and multifocal may be merged into a single class labeled focal.

Finally, the process flow concludes with Step S15 where the margin status is reported, i.e. output, e.g. to a display and/or by saving to a file.

In summary, we have described a computer-automated method for image processing a histological image of a tissue section obtained from a tumor mass extracted by resection and painted with an ink to highlight its surface region. One or two convolutional neural networks are trained to distinguish between tissue classes that distinguish between ink and no-ink as well as tumor and no-tumor. The trained neural network or networks are applied to the histological image to generate an output image whose pixels are assigned to the tissue classes. Positive or negative margin status of the tissue section can then be determined dependent respectively on the presence or absence of tumor-and-ink classified pixels. In addition, the positive and negative margin statuses can be examined further to generate sub-statuses for margin involvement (positive sub-statuses) and margin distance (negative sub-statuses) by computing additional parameters based on classification-specified inter-pixel distances.

Tumor Area Filtering & Ranking

FIG. 7 is a flow diagram of according to an embodiment of the disclosure.

Step S71 provides an image data file containing image data of a WSI, as may have been generated by a slide scanner. It will be appreciated the image data file may include multiple images, e.g. one for each of a plurality of stains, or one for each of a different depth in the sample (a so-called z-stack) obtained by stepping the focal plane of the microscope through a transparent or semi-transparent sample of finite depth.

Step S72 is an optional step where some CNN pre-processing may be performed, as described by way of example further above, such as variance-based analysis, adaptive thresholding, morphological operations and so forth.

Step S73 runs the above-described CNN, in particular as described with reference to Steps S51 to S54 of FIG. 5. A pixel-by-pixel classification of tissue type is performed to mark tumor pixels, followed by segmentation to outline tumors (i.e. tumor areas). The tissue type is a classification by carcinoma type. For the segmentation, it is generally the case that contiguous tumor pixels, i.e. ones that are touching each other or in close proximity to each other, belong to a common tumor. More complex segmentation criteria will however usually be included to improve reliability, e.g. to identify two touching tumors of different pixel classifications, e.g. associated with two different cancerous cell classifications. The CNN assigns each pixel a probability, which is the probability vector representing the probability of the pixel belonging to each of the N classes that the CNN has been trained to detect. For example, in the case of a CNN trained to distinguish between invasive, in situ and non-tumor areas, each pixel will be assigned a vector of length 3. A pixel at location k may have a probability vector [0.1, 0.2, 0.7] indicating there is a 10% probability the pixel is in an invasive area, a 20% probability it is in an in situ area and a 70% probability it is in a non-tumor area.

In Step S74, the data generated by the tumor-finding CNN in Step 73, i.e. the tumor-specific data, is used to compute a set of summary statistics for each tumor. For example, for each tumor, a score may be computed as the mathematical average of the above-mentioned probability values for all the pixels contained in that tumor (area). Some other summary statistic such as median, weighted average, etc. may also be used to compute a score. Other measures may be used for example dimensional or morphological attributes of a tumor, such as tumor area as measured by the number of pixels in the tumor or shape of tumor area or prevalence of a certain pixel classification such as invasive tumor and in situ tumor. Usually for each tumor the average and standard deviation of tumor probability, tumor area and length of the tumors' greatest dimension will be included. Tumor areas are not necessarily from a single slide; they may belong to separate slides, e.g. the tissue samples of two slides may be stained with different stains and thus highlight different classes of tumor cells, so that some tumors are identified in a first slide and other tumors in a second slide. Optionally, more sophisticated scores can be computed. For example, it is possible to predict patient risk using a CNN trained on a combination of histology image data (i.e. tumors identified in image data) and patient-specific genetic (i.e. genomic) data. A CNN of this kind is described in Mobadersany et al 2018. In other implementations, the score can be computed using traditional image processing techniques (e.g. as listed further above in connection with segmentation) applied to the tumors identified by the CNN. For example, shape and texture measures can be combined with genetic data to create a set of statistical measures to include in the summary statistics. A support vector machine or random forest algorithm may use these features to predict risk of metastasis. We define the risk of metastasis as the probability that cells from this tumor will metastasize to other parts of the body. Either way a metastasis risk score will be computed and associated with each tumor area.

Step S75 carries out a filtering of the tumors based on the summary statistics computed and compiled in Step S74. The filter may operate by a simple pass through the list of tumors comparing a the value of a single one of the parameters in the summary statistics, or a compound value derived from a logical combination and/or formula including multiple ones of the parameters present in the summary statistics, with a threshold value and then removing or keeping the tumor object based on the comparison result. For example, the filter, which may be configured by the pathologist or be pre-set, may choose to pass only tumors with a maximum dimension above a threshold value, e.g. 100 micrometers, that have an average probability above a threshold value, e.g. 50%. Another example filter is to pass only tumors classified as invasive and among invasive tumors only those with an average probability above a threshold value of, say, 80%.

Step S76 takes the set of tumors passed by the filter in Step S75 and ranks them in order. A ranking of the tumors can then be carried out based on the summary statistics and applying a set of criteria. Pre-sets of standard ranking approaches may be provided to the user, allowing the user to select one of the pre-sets. Moreover, the user may be provided with a user interface to define which criteria are to be applied. In the case of scalar valued criteria, e.g. based on a length dimension or area or an integer count (e.g. cell count), the user may set threshold values, or value ranges for these criteria. The ranking order may be based on a composite score indicating importance for patient survival, e.g. 5-year survival probability, or be a simple single parameter ranking, e.g. based on a size parameter of the tumor such as area or maximum dimension, or a morphological parameter such as roundness.

Step S77 generates a visualization of the slide image and displays it to the user in a GUI window of a display device. The visualization takes account of the filtering and also the ranking. In particular, what are deemed to be the most important tumors in the WSI are displayed in a clinically relevant way with their summary statistics also being available either in all cases as part of the overall display, or selectively responsive to a GUI command from the user, e.g. 'clicking' with a cursor on a tumor of interest in the WSI to generate a pop-up window showing the statistics for that tumor in tabular or other suitable form. This approach allows potentially significant tumors to be highlighted and presented to the user in a way that provides the user with ranking information among the potentially significant tumors as well as statistical summaries of these tumors. The statistical summaries can present individual parameter values for each tumor, in particular those used as filtering and/or ranking criteria, as well as compound parameters such as a ranking number or significance score that are computed from formulaic and/or Boolean logical combinations of multiple filtering and/or ranking criteria.

Typically, the image displayed will either be in the form of a combined overlay view or a multi-tile view. In an overlay view the raw data (possibly processed) is displayed with the segmentation data overlaid on top, where the segmentation data is translated for the visualization into a shading and/or outline of each tumor. The shading or outlining may be color-coded, e.g. by tumor classification. Non-tumorous areas of tissue may not be marked at all or may be shaded with a color wash of high transparency, e.g. a blue wash. In a multi-tile view, what were the different layers in the overlay view are displayed side-by-side as tiles, so there will be a tile showing raw image data (possibly processed) and segmentation data of the filtered tumor areas. If desired a separate segmentation data tile may be displayed for each tumor classification type. The presentation of the tumor areas in the display takes account of the filtering performed in Step S75 and preferably also the ranking performed in Step S76. Factors such as the tumor scores, the classified tumor type and any other parameters in the summary statistics associated with tumor areas can be used singly or in combination to configure the display.

There are several options for displaying the detected, filtered and ranked tumors to the user.

In a WSI view, one way to display the tumor information is to overlay a series of markers, which may comprise thumbnail images and/or text information, over a low-resolution image of the WSI. The markers can be sorted by, or expressly indicate, a ranking. A pathologist is provided with suitable GUI tools for selecting a tumor through selecting its marker, and optionally also for navigating through the tumors by ranking, both from higher ranked tumors to lower ranked tumors and the other way. Suitable GUI tools include: keyboard shortcuts; keyboard up and down, or left and right, arrow keys, keyboard page up and page down keys, mouse navigation (e.g. scrolling up or down with a scroll wheel) or other input devices (voice navigation, multitouch gesture in a touch sensor, etc.). Selecting the ranking marker in the GUI may prompt display of that tumor's summary statistics, or a subset thereof, and/or display of a higher resolution view of the tumor either in a pop-up linked to the display of the tumor in the low-resolution image, or in a separate, higher resolution viewing pane. The user may cause display of a high, e.g. full native, resolution image of the tumor by a suitable GUI command, such as a keyboard command, a mouse command (e.g. double-click) or other suitable input. A corresponding GUI command is provided to navigate back to a low-resolution WSI view. The visualization application preferably provides GUI controls that permit the user to step through the tumors up or down by ranking order in both low-resolution and high-resolution views.

One example WSI view would be for all tumors that have passed the filter of Step S76 to be displayed (i.e. their segmentation data displayed), together with a ranking marker label 1, 2, 3 etc. Clicking on the ranking marker label (or the tumor) may then generate a pop-up listing a selected set of the summary statistics, in particular those that are used by the filter and/or a thumbnail view of the tumor at a resolution higher than that in the WSI view. Alternatively, the view may be a split-screen view with the overlay image or image tiles being displayed in one part of the screen and a table of the filtered tumors in another part of the screen. The table may be presented initially sorted by ranking, but the GUI may also have the facility to be user re-sortable by any other column, or combination of multiple columns, where the other columns may be any criterion from the summary statistics or filter criteria, such as tumor area, tumor classification, metastatic probability etc. For example, the sorting could be by tumor classification followed by tumor area. In the case of a multi-slide image file, the sorting could be by slide number followed by some other parameter (s).

In a multi-resolution view comprising one viewing pane at lower resolution (e.g. 10× magnification), typically reproducing a WSI, and another viewing pane at higher resolution (e.g. 60× magnification, i.e. 6× or 600% zoom relative to the 10× view). For example, the initial view presented may be a WSI low resolution image pane and a high-resolution image pane centered on the tumor area with the top ranking. A step-through down arrow (or pair of down and up arrows) or other suitable GUI button or button combination, such as a physical or virtual scroll wheel, may then allow the user to step through the filtered tumor areas by ranking one by one. The GUI may allow the user to adjust the resolution in the high-resolution image pane through user input. The GUI may also select the initial resolution for the high-resolution image pane so that the tumor is sized to substantially fill the high-resolution viewing pane.

The visualization application may thus determine what is displayed to the user, what tumors are highlighted with segmentation data and summary statistics and, in the case of a selective view, the time sequence, i.e. order, in which the tumors are displayed to the user.

Another way of displaying the tumor areas that is particularly suited to slide sets is to create a montage where low-resolution images of the tumors along with their summary statistics are displayed as sorted tiles. The sorting may be by way of displaying a one-dimensional (1D) list, or a two-dimensional (2D) grid. It is even possible to arrange the tumors in three dimensions, e.g. with the aid of virtual reality goggles. The user may navigate the 1D list or 2D tile array using keystrokes, mouse scrolling or other input modalities (voice, touch, etc.). Once a tile is selected the pathologist can quickly navigate to a high-resolution version of the tumor in the appropriate slide to make a more in-depth verification of the tumor optionally with comparison to the results of the CNN analysis as presented by the summary statistics and segmentation data, and optionally also perform additional processing on the tumor by applying one or more further analysis algorithms to the tumor that may assist diagnosis.

In Step S78, after viewing the filtered and ranked tumors, the pathologist has the further option of selecting any one of these tumors (or any subset of the ranked tumors, or indeed the full set of filtered tumors) for further study.

In Step S79, this further study is performed. By further study we mean applying one or more additional algorithms to provide further information on the selected tumors to assist with their diagnosis. This may be to help confirm a provisional diagnosis or to make an initial diagnosis for the pathologist to consider as a starting point.

For example, for breast cancer, in Step S78 a pathologist may select for tumors containing invasive breast carcinomas and then in Step S79 apply an algorithm that computes the mitotic count of a tumor. That is, the visualization application includes such an algorithm. Another breast cancer example relevant for image data from an IHC stained slide is to apply an algorithm to compute scores for the expression of one or more diagnostically relevant genes, such as ER, PR, or HER2 in a selected tumor.

In summary, the visualization is configured to prompt the user to examine areas in the image that contain potentially significant tumors. In particular, compared with a traditional visualization application, it is not necessary for the user to perform a manual visual scan over the whole slide area at low resolution, zooming in to, and back out of, a higher resolution view whenever a potential tumor area is encountered. The automated pre-processing of the visualization presented to the pathologist based on CNN-aided filtering and ranking as described above thus reduces the amount of time needed by the pathologist to review a slide and make appropriate diagnoses as well as reducing the chance that an important tumor is missed by human error.

Example Embodiment

In one embodiment, a system for identifying tumors in a histological image is configured to perform a method to identify tumors in a histological image. The method includes receiving a histological image including a two-dimensional array of pixels and applying a convolutional neural network to generate an output image having a two-dimensional array of pixels and a mapping of the pixels in the output image to the pixels of the histology image. The output image is generated by assigning one of a plurality of tissue classes to each pixel, wherein the plurality of tissue classes includes at least one class representing non-tumorous tissue and at least one class representing tumorous tissue.

Next, the system generates a segmentation mask from the output image. The segmentation mask identifies areas occupied by individual tumors. The system also computes summary statistics for each tumor and the system is configured to filter the segmentation mask to select and deselect individual tumors according to the to the summary statistics for each tumor. The system is also configured to create a visualization of the histological image in accordance with the edited segmentation mask and receive a selection of an individual tumor in the filtered segmentation mask and then coordinate execution of an additional computational diagnostic process on the currently selected tumor.

In one embodiment, the additional computational diagnostic process comprises sending a processing task to the additional computational diagnostic process and receiving results of the processing task from the additional computational diagnostic. The additional computational diagnostic process can be executed locally or on a remote processor enabled device communicatively coupled via a data communication network. A portion of the processing task may include the histological image. The processing task may also include metadata related to the histological image and in some circumstances, the metadata related to the histological image may include the segmentation mask. Additionally, the metadata related to the histological image may also include one or more of patient information, stain information, staining protocol information, and scanning protocol information.

CNN Computing Platform

The proposed image processing may be carried out on a variety of computing architectures, in particular ones that are optimized for neural networks, which may be based on CPUs, GPUs, TPUs, FPGAs and/or ASICs. In some embodiments, the neural network is implemented using Google's Tensorflow software library running on Nvidia GPUs from Nvidia Corporation, Santa Clara, California, such as the Tesla K80 GPU. In other embodiments, the neural network can run on generic CPUs. Faster processing can be obtained by a purpose-designed processor for performing CNN calculations, for example the TPU disclosed in Jouppi et al 2017, the full contents of which is incorporated herein by reference.

Figure 8:
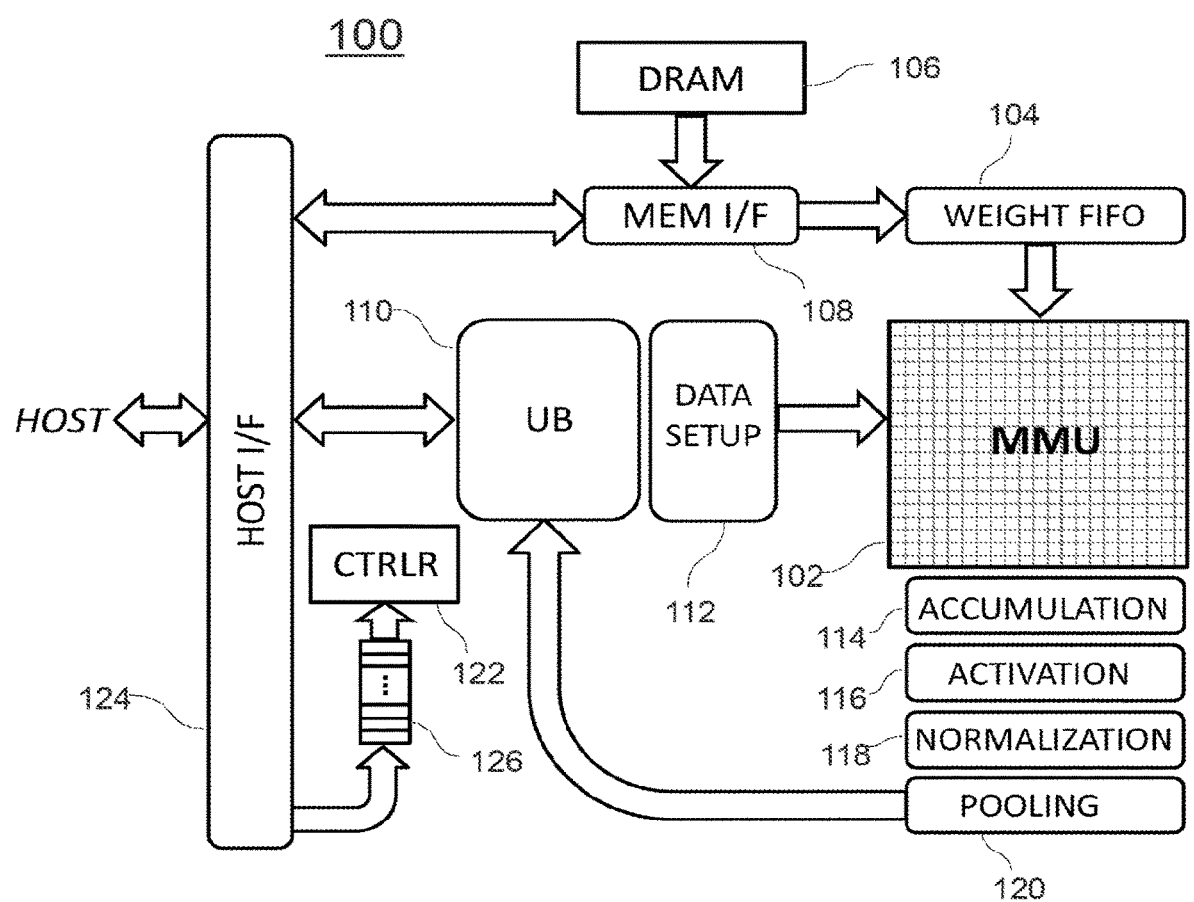
FIG. 8 is a block diagram of a TPU which may be used for performing the computations involved in implementing the neural network architecture of FIGS. 1A and 1B.

FIG. 8 shows the TPU of Jouppi et al 2017, being a simplified reproduction of Jouppi's FIG. 1. The TPU 100 has a systolic matrix multiplication unit (MMU) 102 which contains 256×256 MACs that can perform 8-bit multiply-and-adds on signed or unsigned integers. The weights for the MMU are supplied through a weight FIFO buffer 104 that in turn reads the weights from a memory 106, in the form of an off-chip 8 GB DRAM, via a suitable memory interface 108. A unified buffer (UB) 110 is provided to store the intermediate results. The MMU 102 is connected to receives inputs from the weight FIFO interface 104 and the UB 110 (via a systolic data setup unit 112) and outputs the 16-bit products of the MMU processing to an accumulator unit 114. An activation unit 116 performs nonlinear functions on the data held in the accumulator unit 114. After further processing by a normalizing unit 118 and a pooling unit 120, the intermediate results are sent to the UB 110 for resupply to the MMU 102 via the data setup unit 112. The pooling unit 120 may perform maximum pooling (i.e. maxpooling) or average pooling as desired. A programmable DMA controller 122 transfers data to or from the TPU's host computer and the UB 110. The TPU instructions are sent from the host computer to the controller 122 via a host interface 124 and an instruction buffer 126.

It will be understood that the computing power used for running the neural network, whether it be based on CPUs, GPUs or TPUs, may be hosted locally in a clinical network, e.g. the one described below, or remotely in a data center.

Network & Computing & Scanning Environment

The proposed computer-automated method operates in the context of a laboratory information system (LIS) which in turn is typically part of a larger clinical network environment, such as a hospital information system (HIS) or picture archiving and communication system (PACS). In the LIS, the WSIs will be retained in a database, typically a patient information database containing the electronic medical records of individual patients. The WSIs will be taken from stained tissue samples mounted on slides, the slides bearing printed barcode labels by which the WSIs are tagged with suitable metadata, since the microscopes acquiring the WSIs are equipped with barcode readers. From a hardware perspective, the LIS will be a conventional computer network, such as a local area network (LAN) with wired and wireless connections as desired.

Figure 9:
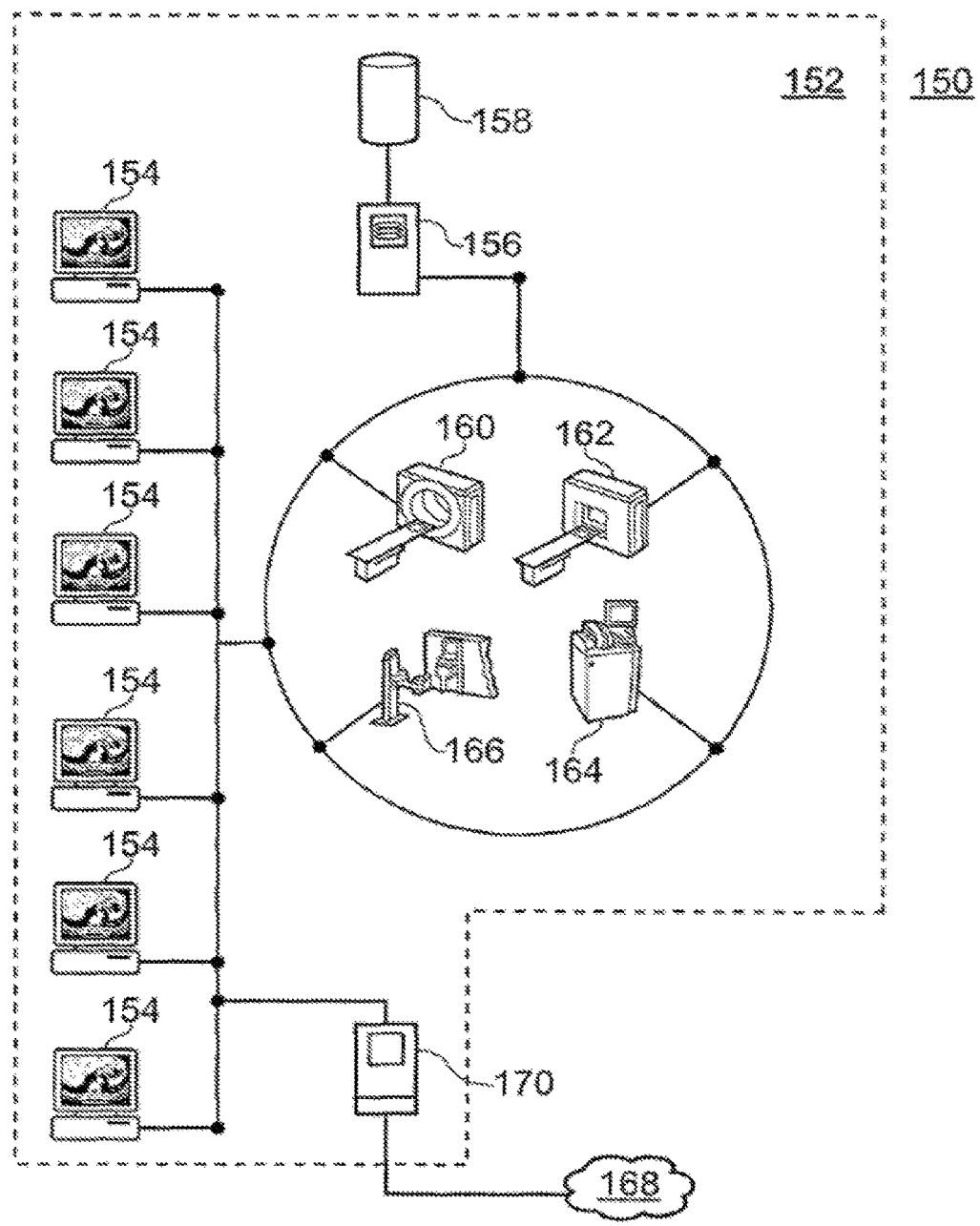
FIG. 9 shows an example computer network which can be used in conjunction with embodiments of the invention.

FIG. 9 shows an example computer network which can be used in conjunction with embodiments of the invention. The network 150 comprises a LAN in a hospital 152. The hospital 152 is equipped with a number of workstations 154 which each have access, via the local area network, to a hospital computer server 156 having an associated storage device 158. A LIS, HIS or PACS archive is stored on the storage device 158 so that data in the archive can be accessed from any of the workstations 154. One or more of the workstations 154 has access to a graphics card and to software for computer-implementation of methods of generating images as described hereinbefore. The software may be stored locally at the or each workstation 154 or may be stored remotely and downloaded over the network 150 to a workstation 154 when needed. In other example, methods embodying the invention may be executed on the computer server with the workstations 154 operating as terminals. For example, the workstations may be configured to receive user input defining a desired histological image data set and to display resulting images while CNN analysis is performed elsewhere in the system. Also, a number of histological and other medical imaging devices 160, 162, 164, 166 are connected to the hospital computer server 156. Image data collected with the devices 160, 162, 164, 166 can be stored directly into the LIS, HIS or PACS archive on the storage device 156. Thus, histological images can be viewed and processed immediately after the corresponding histological image data are recorded. The local area network is connected to the Internet 168 by a hospital Internet server 170, which allows remote access to the LIS, HIS or PACS archive. This is of use for remote accessing of the data and for transferring data between hospitals, for example, if a patient is moved, or to allow external research to be undertaken.

Figure 10:
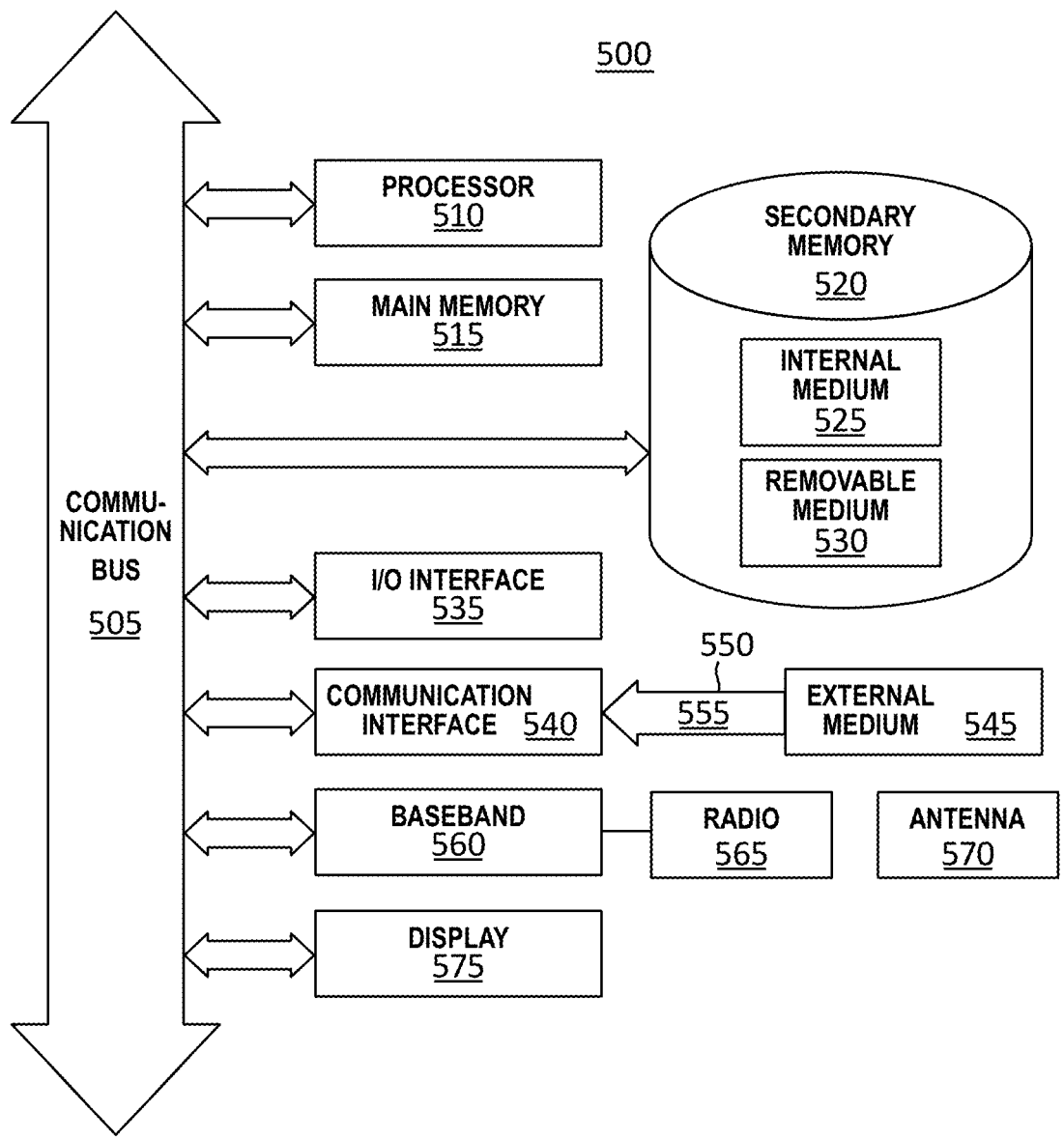
FIG. 10 is a block diagram of a computing apparatus that may be used for example as the host computer for the TPU of FIG. 10.

FIG. 10 is a block diagram illustrating an example computing apparatus 500 that may be used in connection with various embodiments described herein. For example, computing apparatus 500 may be used as a computing node in the above-mentioned LIS or PACS system, for example a host computer from which CNN processing is carried out in conjunction with a suitable GPU, or the TPU shown in FIG. 8.

Computing apparatus 500 can be a server or any conventional personal computer, or any other processor-enabled device that is capable of wired or wireless data communication. Other computing apparatus, systems and/or architectures may be also used, including devices that are not capable of wired or wireless data communication, as will be clear to those skilled in the art.

Computing apparatus 500 preferably includes one or more processors, such as processor 510. The processor 510 may be for example a CPU, GPU, TPU or arrays or combinations thereof such as CPU and TPU combinations or CPU and GPU combinations. Additional processors may be provided, such as an auxiliary processor to manage input/output, an auxiliary processor to perform floating point mathematical operations (e.g. a TPU), a special-purpose microprocessor having an architecture suitable for fast execution of signal processing algorithms (e.g., digital signal processor, image processor), a slave processor subordinate to the main processing system (e.g., back-end processor), an additional microprocessor or controller for dual or multiple processor systems, or a coprocessor. Such auxiliary processors may be discrete processors or may be integrated with the processor 510. Examples of CPUs which may be used with computing apparatus 500 are, the Pentium processor, Core i7 processor, and Xeon processor, all of which are available from Intel Corporation of Santa Clara, California. An example GPU which may be used with computing apparatus 500 is Tesla K80 GPU of Nvidia Corporation, Santa Clara, California.

Processor 510 is connected to a communication bus 505. Communication bus 505 may include a data channel for facilitating information transfer between storage and other peripheral components of computing apparatus 500. Communication bus 505 further may provide a set of signals used for communication with processor 510, including a data bus, address bus, and control bus (not shown). Communication bus 505 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPM), IEEE 696/S-100, and the like.

Computing apparatus 500 preferably includes a main memory 515 and may also include a secondary memory 520. Main memory 515 provides storage of instructions and data for programs executing on processor 510, such as one or more of the functions and/or modules discussed above. It should be understood that computer readable program instructions stored in the memory and executed by processor 510 may be assembler instructions, instruction-set-architecture (ISA) instructions, machine instructions, machine dependent instructions, microcode, firmware instructions, state-setting data, configuration data for integrated circuitry, or either source code or object code written in and/or compiled from any combination of one or more programming languages, including without limitation Smalltalk, C/C++, Java, JavaScript, Perl, Visual Basic, .NET, and the like. Main memory 515 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Secondary memory 520 may optionally include an internal memory 525 and/or a removable medium 530. Removable medium 530 is read from and/or written to in any well-known manner. Removable storage medium 530 may be, for example, a magnetic tape drive, a compact disc (CD) drive, a digital versatile disc (DVD) drive, other optical drive, a flash memory drive, etc.

Removable storage medium 530 is a non-transitory computer-readable medium having stored thereon computer-executable code (i.e., software) and/or data. The computer software or data stored on removable storage medium 530 is read into computing apparatus 500 for execution by processor 510.

The secondary memory 520 may include other similar elements for allowing computer programs or other data or instructions to be loaded into computing apparatus 500. Such means may include, for example, an external storage medium 545 and a communication interface 540, which allows software and data to be transferred from external storage medium 545 to computing apparatus 500. Examples of external storage medium 545 may include an external hard disk drive, an external optical drive, an external magneto-optical drive, etc. Other examples of secondary memory 520 may include semiconductor-based memory such as programmable read-only memory (PROM), erasable programmable read-only memory (EPROM), electrically erasable read-only memory (EEPROM), or flash memory (block-oriented memory similar to EEPROM).

As mentioned above, computing apparatus 500 may include a communication interface 540. Communication interface 540 allows software and data to be transferred between computing apparatus 500 and external devices (e.g. printers), networks, or other information sources. For example, computer software or executable code may be transferred to computing apparatus 500 from a network server via communication interface 540. Examples of communication interface 540 include a built-in network adapter, network interface card (MC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device. Communication interface 540 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 540 are generally in the form of electrical communication signals 555. These signals 555 may be provided to communication interface 540 via a communication channel 550. In an embodiment, communication channel 550 may be a wired or wireless network, or any variety of other communication links. Communication channel 550 carries signals 555 and can be implemented using a variety of wired or wireless communication means including wire or cable, fiber optics, conventional phone line, cellular phone link, wireless data communication link, radio frequency ("RF") link, or infrared link, just to name a few.

Computer-executable code (i.e., computer programs or software) is stored in main memory 515 and/or the secondary memory 520. Computer programs can also be received via communication interface 540 and stored in main memory 515 and/or secondary memory 520. Such computer programs, when executed, enable computing apparatus 500 to perform the various functions of the disclosed embodiments as described elsewhere herein.

In this document, the term "computer-readable medium" is used to refer to any non-transitory computer-readable storage media used to provide computer-executable code (e.g., software and computer programs) to computing apparatus 500. Examples of such media include main memory 515, secondary memory 520 (including internal memory 525, removable medium 530, and external storage medium 545), and any peripheral device communicatively coupled with communication interface 540 (including a network information server or other network device). These non-transitory computer-readable media are means for providing executable code, programming instructions, and software to computing apparatus 500. In an embodiment that is implemented using software, the software may be stored on a computer-readable medium and loaded into computing apparatus 500 by way of removable medium 530, I/O interface 535, or communication interface 540. In such an embodiment, the software is loaded into computing apparatus 500 in the form of electrical communication signals 555. The software, when executed by processor 510, preferably causes processor 510 to perform the features and functions described elsewhere herein.

I/O interface 535 provides an interface between one or more components of computing apparatus 500 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

Computing apparatus 500 also includes optional wireless communication components that facilitate wireless communication over a voice network and/or a data network. The wireless communication components comprise an antenna system 570, a radio system 565, and a baseband system 560. In computing apparatus 500, radio frequency (RF) signals are transmitted and received over the air by antenna system 570 under the management of radio system 565.

Antenna system 570 may comprise one or more antennae and one or more multiplexors (not shown) that perform a switching function to provide antenna system 570 with transmit and receive signal paths. In the receive path, received RF signals can be coupled from a multiplexor to a low noise amplifier (not shown) that amplifies the received RF signal and sends the amplified signal to radio system 565.

Radio system 565 may comprise one or more radios that are configured to communicate over various frequencies. In an embodiment, radio system 565 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 565 to baseband system 560.

If the received signal contains audio information, then baseband system 560 decodes the signal and converts it to an analog signal. Then the signal is amplified and sent to a speaker. Baseband system 560 also receives analog audio signals from a microphone. These analog audio signals are converted to digital signals and encoded by baseband system 560. Baseband system 560 also codes the digital signals for transmission and generates a baseband transmit audio signal that is routed to the modulator portion of radio system 565. The modulator mixes the baseband transmit audio signal with an RF carrier signal generating an RF transmit signal that is routed to antenna system 570 and may pass through a power amplifier (not shown). The power amplifier amplifies the RF transmit signal and routes it to antenna system 570 where the signal is switched to the antenna port for transmission.

Baseband system 560 is also communicatively coupled with processor 510, which may be a central processing unit (CPU). Processor 510 has access to data storage areas 515 and 520. Processor 510 is preferably configured to execute instructions (i.e., computer programs or software) that can be stored in main memory 515 or secondary memory 520. Computer programs can also be received from baseband processor 560 and stored in main memory 510 or in secondary memory 520 or executed upon receipt. Such computer programs, when executed, enable computing apparatus 500 to perform the various functions of the disclosed embodiments. For example, data storage areas 515 or 520 may include various software modules.

The computing apparatus further comprises a display 575 directly attached to the communication bus 505 which may be provided instead of or addition to any display connected to the I/O interface 535 referred to above.

Various embodiments may also be implemented primarily in hardware using, for example, components such as application specific integrated circuits (ASICs), programmable logic arrays (PLA), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit, or step is for ease of description. Specific functions or steps can be moved from one module, block, or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA, or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

A computer readable storage medium, as referred to herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

Embodiments of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The illustrated flowcharts and block diagrams illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Apparatus and methods embodying the invention are capable of being hosted in and delivered by a cloud computing environment. Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

It will be clear to one skilled in the art that many improvements and modifications can be made to the foregoing exemplary embodiment without departing from the scope of the present disclosure.

Figure 11A:
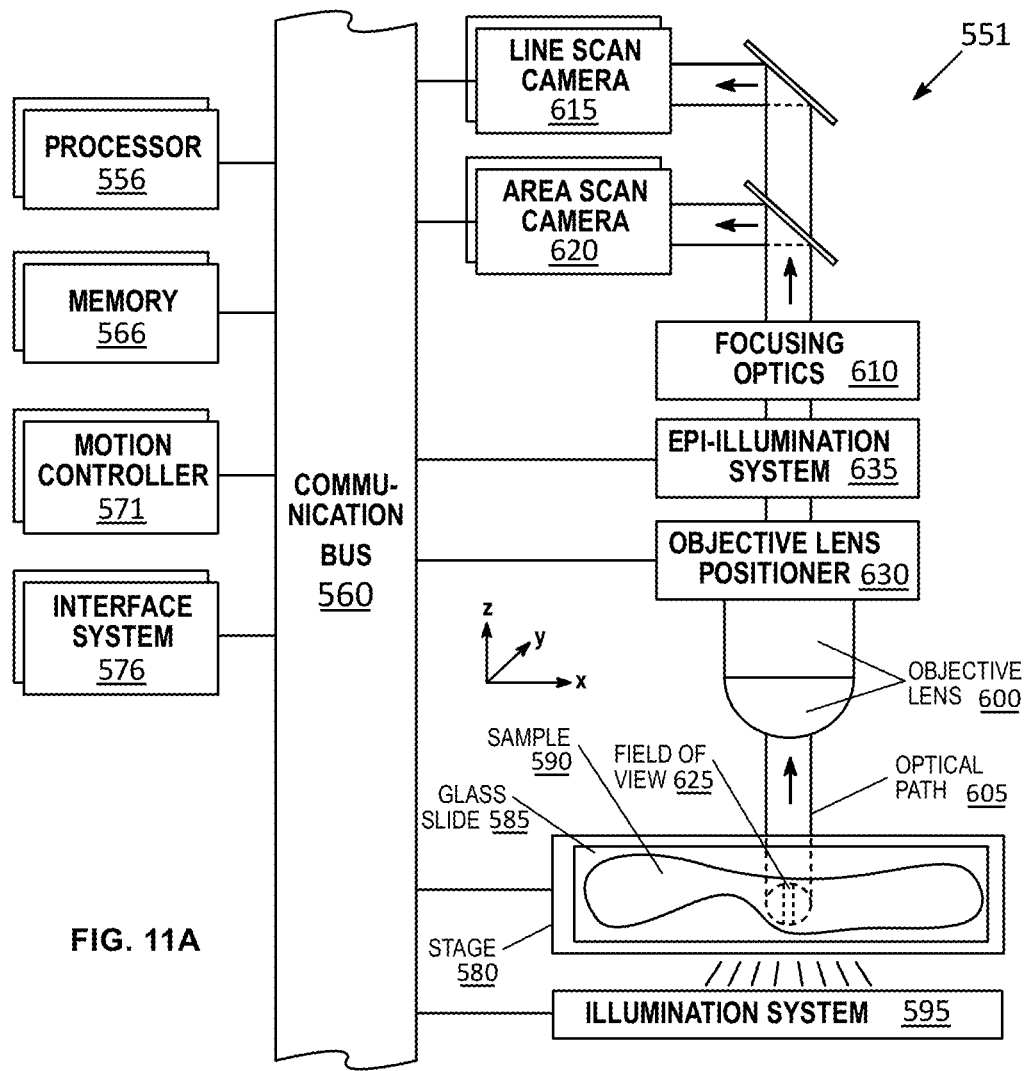
FIG. 11A is a block diagram illustrating an example processor enabled device 550 that may be used in connection with various embodiments described herein.

FIG. 11A is a block diagram illustrating an example processor enabled device 551 that may be used in connection with various embodiments described herein. Alternative forms of the device 551 may also be used as will be understood by the skilled artisan. In the illustrated embodiment, the device 551 is presented as a digital imaging device (also referred to herein as a scanner system or a scanning system) that comprises one or more processors 556, one or more memories 566, one or more motion controllers 571, one or more interface systems 576, one or more movable stages 580 that each support one or more glass slides 585 with one or more samples 590, one or more illumination systems 595 that illuminate the sample, one or more objective lenses 600 that each define an optical path 605 that travels along an optical axis, one or more objective lens positioners 630, one or more optional epi-illumination systems 635 (e.g., included in a fluorescence scanner system), one or more focusing optics 610, one or more line scan cameras 615 and/or one or more area scan cameras 620, each of which define a separate field of view 625 on the sample 590 and/or glass slide 585. The various elements of the scanner system 551 are communicatively coupled via one or more communication busses 560. Although there may be one or more of each of the various elements of the scanner system 551, for simplicity in the description that follows, these elements will be described in the singular except when needed to be described in the plural to convey the appropriate information.

The one or more processors 556 may include, for example, a central processing unit ("CPU") and a separate graphics processing unit ("GPU") capable of processing instructions in parallel or the one or more processors 556 may include a multicore processor capable of processing instructions in parallel. Additional separate processors may also be provided to control particular components or perform particular functions such as image processing. For example, additional processors may include an auxiliary processor to manage data input, an auxiliary processor to perform floating point mathematical operations, a special-purpose processor having an architecture suitable for fast execution of signal processing algorithms (e.g., digital signal processor), a slave processor subordinate to the main processor (e.g., back-end processor), an additional processor for controlling the line scan camera 615, the stage 580, the objective lens 225, and/or a display (not shown). Such additional processors may be separate discrete processors or may be integrated with the processor 556.

The memory 566 provides storage of data and instructions for programs that can be executed by the processor 556. The memory 566 may include one or more volatile and persistent computer-readable storage mediums that store the data and instructions, for example, a random access memory, a read only memory, a hard disk drive, removable storage drive, and the like. The processor 556 is configured to execute instructions that are stored in memory 566 and communicate via communication bus 560 with the various elements of the scanner system 551 to carry out the overall function of the scanner system 551.

The one or more communication busses 560 may include a communication bus 560 that is configured to convey analog electrical signals and may include a communication bus 560 that is configured to convey digital data. Accordingly, communications from the processor 556, the motion controller 571, and/or the interface system 576 via the one or more communication busses 560 may include both electrical signals and digital data. The processor 556, the motion controller 571, and/or the interface system 576 may also be configured to communicate with one or more of the various elements of the scanning system 551 via a wireless communication link.

The motion control system 571 is configured to precisely control and coordinate XYZ movement of the stage 580 and the objective lens 600 (e.g., via the objective lens positioner 630). The motion control system 571 is also configured to control movement of any other moving part in the scanner system 551. For example, in a fluorescence scanner embodiment, the motion control system 571 is configured to coordinate movement of optical filters and the like in the epi-illumination system 635.

The interface system 576 allows the scanner system 551 to interface with other systems and human operators. For example, the interface system 576 may include a user interface to provide information directly to an operator and/or to allow direct input from an operator. The interface system 576 is also configured to facilitate communication and data transfer between the scanning system 551 and one or more external devices that are directly connected (e.g., a printer, removable storage medium) or external devices such as an image server system, an operator station, a user station, and an administrative server system that are connected to the scanner system 551 via a network (not shown).

The illumination system 595 is configured to illuminate a portion of the sample 590. The illumination system may include, for example, a light source and illumination optics. The light source could be a variable intensity halogen light source with a concave reflective mirror to maximize light output and a KG-1 filter to suppress heat. The light source could also be any type of arc-lamp, laser, or other source of light. In one embodiment, the illumination system 595 illuminates the sample 590 in transmission mode such that the line scan camera 615 and/or area scan camera 620 sense optical energy that is transmitted through the sample 590. Alternatively, or in combination, the illumination system 595 may also be configured to illuminate the sample 590 in reflection mode such that the line scan camera 615 and/or area scan camera 620 sense optical energy that is reflected from the sample 590. Overall, the illumination system 595 is configured to be suitable for interrogation of the microscopic sample 590 in any known mode of optical microscopy.

In one embodiment, the scanner system 551 optionally includes an epi-illumination system 635 to optimize the scanner system 551 for fluorescence scanning. Fluorescence scanning is the scanning of samples 590 that include fluorescence molecules, which are photon sensitive molecules that can absorb light at a specific wavelength (excitation). These photon sensitive molecules also emit light at a higher wavelength (emission). Because the efficiency of this photoluminescence phenomenon is very low, the amount of emitted light is often very low. This low amount of emitted light typically frustrates conventional techniques for scanning and digitizing the sample 590 (e.g., transmission mode microscopy). Advantageously, in an optional fluorescence scanner system embodiment of the scanner system 551, use of a line scan camera 615 that includes multiple linear sensor arrays (e.g., a time delay integration ("TDI") line scan camera) increases the sensitivity to light of the line scan camera by exposing the same area of the sample 590 to each of the multiple linear sensor arrays of the line scan camera 615. This is particularly useful when scanning faint fluorescence samples with low emitted light.

Accordingly, in a fluorescence scanner system embodiment, the line scan camera 615 is preferably a monochrome TDI line scan camera. Advantageously, monochrome images are ideal in fluorescence microscopy because they provide a more accurate representation of the actual signals from the various channels present on the sample. As will be understood by those skilled in the art, a fluorescence sample 590 can be labeled with multiple florescence dyes that emit light at different wavelengths, which are also referred to as "channels."

Furthermore, because the low and high end signal levels of various fluorescence samples present a wide spectrum of wavelengths for the line scan camera 615 to sense, it is desirable for the low and high end signal levels that the line scan camera 615 can sense to be similarly wide. Accordingly, in a fluorescence scanner embodiment, a line scan camera 615 used in the fluorescence scanning system 551 is a monochrome 10 bit 64 linear array TDI line scan camera. It should be noted that a variety of bit depths for the line scan camera 615 can be employed for use with a fluorescence scanner embodiment of the scanning system 551.

The movable stage 580 is configured for precise XY movement under control of the processor 556 or the motion controller 571. The movable stage may also be configured for movement in Z under control of the processor 556 or the motion controller 571. The moveable stage is configured to position the sample in a desired location during image data capture by the line scan camera 615 and/or the area scan camera. The moveable stage is also configured to accelerate the sample 590 in a scanning direction to a substantially constant velocity and then maintain the substantially constant velocity during image data capture by the line scan camera 615. In one embodiment, the scanner system 551 may employ a high precision and tightly coordinated XY grid to aid in the location of the sample 590 on the movable stage 580. In one embodiment, the movable stage 580 is a linear motor based XY stage with high precision encoders employed on both the X and the Y axis. For example, very precise nanometer encoders can be used on the axis in the scanning direction and on the axis that is in the direction perpendicular to the scanning direction and on the same plane as the scanning direction. The stage is also configured to support the glass slide 585 upon which the sample 590 is disposed.

The sample 590 can be anything that may be interrogated by optical microscopy. For example, a glass microscope slide 585 is frequently used as a viewing substrate for specimens that include tissues and cells, chromosomes, DNA, protein, blood, bone marrow, urine, bacteria, beads, biopsy materials, or any other type of biological material or substance that is either dead or alive, stained or unstained, labeled or unlabeled. The sample 590 may also be an array of any type of DNA or DNA-related material such as cDNA or RNA or protein that is deposited on any type of slide or other substrate, including any and all samples commonly known as a microarrays. The sample 590 may be a microtiter plate, for example a 96-well plate. Other examples of the sample 590 include integrated circuit boards, electrophoresis records, petri dishes, film, semiconductor materials, forensic materials, or machined parts.

Objective lens 600 is mounted on the objective positioner 630 which, in one embodiment, may employ a very precise linear motor to move the objective lens 600 along the optical axis defined by the objective lens 600. For example, the linear motor of the objective lens positioner 630 may include a 50 nanometer encoder. The relative positions of the stage 580 and the objective lens 600 in XYZ axes are coordinated and controlled in a closed loop manner using motion controller 571 under the control of the processor 556 that employs memory 566 for storing information and instructions, including the computer-executable programmed steps for overall scanning system 551 operation.

In one embodiment, the objective lens 600 is a plan apochromatic ("APO") infinity corrected objective with a numerical aperture corresponding to the highest spatial resolution desirable, where the objective lens 600 is suitable for transmission mode illumination microscopy, reflection mode illumination microscopy, and/or epi-illumination mode fluorescence microscopy (e.g., an Olympus 40×, 0.75NA or 20×, 0.75 NA). Advantageously, objective lens 600 is capable of correcting for chromatic and spherical aberrations. Because objective lens 600 is infinity corrected, focusing optics 610 can be placed in the optical path 605 above the objective lens 600 where the light beam passing through the objective lens becomes a collimated light beam. The focusing optics 610 focus the optical signal captured by the objective lens 600 onto the light-responsive elements of the line scan camera 615 and/or the area scan camera 620 and may include optical components such as filters, magnification changer lenses, etc. The objective lens 600 combined with focusing optics 610 provides the total magnification for the scanning system 551. In one embodiment, the focusing optics 610 may contain a tube lens and an optional 2× magnification changer. Advantageously, the 2× magnification changer allows a native 20X objective lens 600 to scan the sample 590 at 40× magnification.

The line scan camera 615 comprises at least one linear array of picture elements ("pixels"). The line scan camera may be monochrome or color. Color line scan cameras typically have at least three linear arrays, while monochrome line scan cameras may have a single linear array or plural linear arrays. Any type of singular or plural linear array, whether packaged as part of a camera or custom-integrated into an imaging electronic module, can also be used. For example, 3 linear array ("red-green-blue" or "RGB") color line scan camera or a 96 linear array monochrome TDI may also be used. TDI line scan cameras typically provide a substantially better signal-to-noise ratio ("SNR") in the output signal by summing intensity data from previously imaged regions of a specimen, yielding an increase in the SNR that is in proportion to the square-root of the number of integration stages. TDI line scan cameras comprise multiple linear arrays, for example, TDI line scan cameras are available with 24, 32, 48, 64, 96, or even more linear arrays. The scanner system 551 also supports linear arrays that are manufactured in a variety of formats including some with 512 pixels, some with 1024 pixels, and others having as many as 4096 pixels. Similarly, linear arrays with a variety of pixel sizes can also be used in the scanner system 551. The salient requirement for the selection of any type of line scan camera 615 is that the motion of the stage 580 can be synchronized with the line rate of the line scan camera 615 so that the stage 580 can be in motion with respect to the line scan camera 615 during the digital image capture of the sample 590.

The image data generated by the line scan camera 615 is stored a portion of the memory 566 and processed by the processor 556 to generate a contiguous digital image of at least a portion of the sample 590. The contiguous digital image can be further processed by the processor 556 and the revised contiguous digital image can also be stored in the memory 566.

In an embodiment with two or more line scan cameras 615, at least one of the line scan cameras 615 can be configured to function as a focusing sensor that operates in combination with at least one of the line scan cameras 615 that is configured to function as an imaging sensor. The focusing sensor can be logically positioned on the same optical axis as the imaging sensor or the focusing sensor may be logically positioned before or after the imaging sensor with respect to the scanning direction of the scanner system 551. In such an embodiment with at least one line scan camera 615 functioning as a focusing sensor, the image data generated by the focusing sensor is stored in a portion of the memory 566 and processed by the one or more processors 556 to generate focus information to allow the scanner system 551 to adjust the relative distance between the sample 590 and the objective lens 600 to maintain focus on the sample during scanning. Additionally, in one embodiment the at least one line scan camera 615 functioning as a focusing sensor may be oriented such that each of a plurality of individual pixels of the focusing sensor is positioned at a different logical height along the optical path 605.

In operation, the various components of the scanner system 551 and the programmed modules stored in memory 566 enable automatic scanning and digitizing of the sample 590, which is disposed on a glass slide 585. The glass slide 585 is securely placed on the movable stage 580 of the scanner system 551 for scanning the sample 590. Under control of the processor 556, the movable stage 580 accelerates the sample 590 to a substantially constant velocity for sensing by the line scan camera 615, where the speed of the stage is synchronized with the line rate of the line scan camera 615. After scanning a stripe of image data, the movable stage 580 decelerates and brings the sample 590 to a substantially complete stop. The movable stage 580 then moves orthogonal to the scanning direction to position the sample 590 for scanning of a subsequent stripe of image data, e.g., an adjacent stripe. Additional stripes are subsequently scanned until an entire portion of the sample 590 or the entire sample 590 is scanned.

For example, during digital scanning of the sample 590, a contiguous digital image of the sample 590 is acquired as a plurality of contiguous fields of view that are combined together to form an image strip. A plurality of adjacent image strips are similarly combined together to form a contiguous digital image of a portion or the entire sample 590. The scanning of the sample 590 may include acquiring vertical image strips or horizontal image strips. The scanning of the sample 590 may be either top-to-bottom, bottomto-top, or both (bi-directional) and may start at any point on the sample. Alternatively, the scanning of the sample 590 may be either left-to-right, right-to-left, or both (bi-directional) and may start at any point on the sample. Additionally, it is not necessary that image strips be acquired in an adjacent or contiguous manner. Furthermore, the resulting image of the sample 590 may be an image of the entire sample 590 or only a portion of the sample 590.

In one embodiment, computer-executable instructions (e.g., programmed modules and software) are stored in the memory 566 and, when executed, enable the scanning system 551 to perform the various functions described herein. In this description, the term "computer-readable storage medium" is used to refer to any media used to store and provide computer executable instructions to the scanning system 551 for execution by the processor 556. Examples of these media include memory 566 and any removable or external storage medium (not shown) communicatively coupled with the scanning system 551 either directly or indirectly, for example via a network (not shown).

Figure 11B:
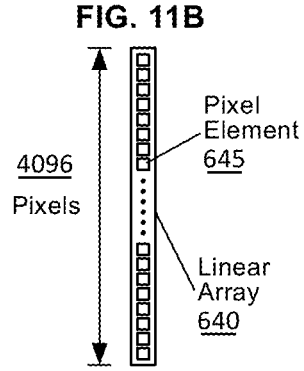
FIG. 11B is a block diagram illustrating an example line scan camera having a single linear array.

FIG. 11B illustrates a line scan camera having a single linear array 640, which may be implemented as a charge coupled device ("CCD") array. The single linear array 640 comprises a plurality of individual pixels 645. In the illustrated embodiment, the single linear array 640 has 4096 pixels. In alternative embodiments, linear array 640 may have more or fewer pixels. For example, common formats of linear arrays include 512, 1024, and 4096 pixels. The pixels 645 are arranged in a linear fashion to define a field of view 625 for the linear array 640. The size of the field of view varies in accordance with the magnification of the scanner system 551.

Figure 11C:
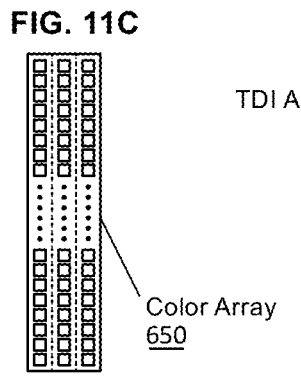
FIG. 11C is a block diagram illustrating an example line scan camera having three linear arrays.

FIG. 11C illustrates a line scan camera having three linear arrays, each of which may be implemented as a CCD array. The three linear arrays combine to form a color array 650. In one embodiment, each individual linear array in the color array 650 detects a different color intensity, for example red, green, or blue. The color image data from each individual linear array in the color array 650 is combined to form a single field of view 625 of color image data.

Figure 11D:
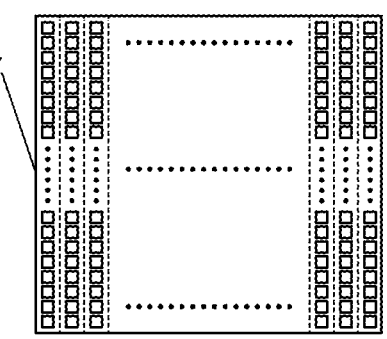
FIG. 11D is a block diagram illustrating an example line scan camera having a plurality of linear arrays.

FIG. 11D illustrates a line scan camera having a plurality of linear arrays, each of which may be implemented as a CCD array. The plurality of linear arrays combine to form a TDI array 655. Advantageously, a TDI line scan camera may provide a substantially better SNR in its output signal by summing intensity data from previously imaged regions of a specimen, yielding an increase in the SNR that is in proportion to the square-root of the number of linear arrays (also referred to as integration stages). A TDI line scan camera may comprise a larger variety of numbers of linear arrays, for example common formats of TDI line scan cameras include 24, 32, 48, 64, 96, 120 and even more linear arrays.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A computer apparatus for identifying tumors in a histological image, comprising:
    a memory configured to store computer-executable instructions; and
    a hardware processor in communication with the memory, wherein the computer-executable instructions, when executed by the processor, configure the processor to perform a method comprising:
        generating, from an output image, a segmentation mask having areas occupied by individual tumors in the output image marked in the segmentation mask;
        computing statistics for each tumor marked in the segmentation mask; and
        applying a filter to the statistics of the tumors to edit the segmentation mask, wherein application of the filter selects and deselects tumors according to the filter to edit the segmentation mask to remove insignificant tumors; wherein:
        the output image comprises an array of pixels, each pixel in the output image being assigned to one of a plurality of tissue classes;
        the output image is generated by a convolutional neural network based on the histological image by performing acts comprising:
            extracting image patches from the histological image, the image patches being area portions of the histological image having a size defined by numbers of pixels in width and height;
            providing the convolutional neural network with a set of weights and a plurality of channels, each channel corresponding to one of the plurality of tissue classes;
            inputting each image patch as an input image patch into the convolutional neural network;
            performing multi-stage convolution to generate convolution layers of ever decreasing dimensions up to and including a final convolution layer of minimum dimensions, followed by multi-stage transpose convolution to reverse the convolutions by generating deconvolution layers of ever increasing dimensions until a layer is recovered matched in size to the input image patch, each pixel in the recovered layer containing a probability of belonging to each of the tissue classes; and
            assigning the tissue class to each pixel of the recovered layer based on said probabilities to arrive at an output image patch.

2. The apparatus of claim 1, wherein the method further comprises:
    providing the convolutional neural network with at least one skip connection, each of which takes intermediate results from at least one of the convolution layers of larger dimensions than the final convolution layer and subjects those results to as many transpose convolutions as needed, which may be none, one or more than one, to obtain at least one further recovered layer matched in size to the input image patch; and
    prior to said step of assigning a tissue class to each pixel, further processing the recovered layer to combine it with the at least one further recovered layers in order to recompute the probabilities to take account of the at least one skip connection.

3. A computer apparatus for identifying tumors in a histological image, comprising:
- a memory configured to store computer-executable instructions; and
- a hardware processor in communication with the memory, wherein the computer-executable instructions, when executed by the processor, configure the processor to perform a method comprising:
  - generating, from an output image, a segmentation mask having areas occupied by individual tumors in the output image marked in the segmentation mask;
  - computing statistics for each tumor marked in the segmentation mask; and
  - applying a filter to the statistics of the tumors to edit the segmentation mask, wherein application of the filter selects and deselects tumors according to the filter to edit the segmentation mask to remove insignificant tumors;
- wherein the histological image is a composite including a plurality of histological images obtained from differently stained, adjacent sections of a region of tissue.

4. A computer apparatus for identifying tumors in a histological image, comprising:
- a memory configured to store computer-executable instructions; and
- a hardware processor in communication with the memory, wherein the computer-executable instructions, when executed by the processor, configure the processor to perform a method comprising:
  - generating, from an output image, a segmentation mask having areas occupied by individual tumors in the output image marked in the segmentation mask;
  - computing statistics for each tumor marked in the segmentation mask; and
  - applying a filter to the statistics of the tumors to edit the segmentation mask, wherein application of the filter selects and deselects tumors according to the filter to edit the segmentation mask to remove insignificant tumors;
- wherein the method further comprises:
  - creating a visualization of the histological image in accordance with the edited segmentation mask;
  - receiving a selection of an individual tumor in the edited segmentation mask; and
  - executing an additional computational diagnostic process on the selected individual tumor.

5. A method for identifying tumors in a histological image, comprising:
- generating, from an output image, a segmentation mask having areas occupied by individual tumors in the output image marked in the segmentation mask;
- computing statistics for each tumor marked in the segmentation mask; and
- applying a filter to the statistics of the tumors to edit the segmentation mask, wherein application of the filter selects and deselects tumors according to the filter to edit the segmentation mask to remove insignificant tumors;
- wherein:
  - the output image comprises an array of pixels, each pixel in the output image being assigned to one of a plurality of tissue classes;
  - the output image is generated by a convolutional neural network based on the histological image by performing acts comprising:
    - extracting image patches from the histological image, the image patches being area portions of the histological image having a size defined by numbers of pixels in width and height;
    - providing the convolutional neural network with a set of weights and a plurality of channels, each channel corresponding to one of the plurality of tissue classes;
    - inputting each image patch as an input image patch into the convolutional neural network;
    - performing multi-stage convolution to generate convolution layers of ever decreasing dimensions up to and including a final convolution layer of minimum dimensions, followed by multi-stage transpose convolution to reverse the convolutions by generating deconvolution layers of ever increasing dimensions until a layer is recovered matched in size to the input image patch, each pixel in the recovered layer containing a probability of belonging to each of the tissue classes; and
    - assigning the tissue class to each pixel of the recovered layer based on said probabilities to arrive at an output image patch.

6. The method of claim 5, wherein the method further comprises:
- providing the convolutional neural network with at least one skip connection, each of which takes intermediate results from at least one of the convolution layers of larger dimensions than the final convolution layer and subjects those results to as many transpose convolutions as needed, which may be none, one or more than one, to obtain at least one further recovered layer matched in size to the input image patch; and
- prior to said step of assigning a tissue class to each pixel, further processing the recovered layer to combine it with the at least one further recovered layers in order to recompute the probabilities to take account of the at least one skip connection.

7. A method for identifying tumors in a histological image, comprising:
- generating, from an output image, a segmentation mask having areas occupied by individual tumors in the output image marked in the segmentation mask;
- computing statistics for each tumor marked in the segmentation mask; and
- applying a filter to the statistics of the tumors to edit the segmentation mask, wherein application of the filter selects and deselects tumors according to the filter to edit the segmentation mask to remove insignificant tumors;
- wherein the histological image is a composite including a plurality of histological images obtained from differently stained, adjacent sections of a region of tissue.

8. A method for identifying tumors in a histological image, comprising:
- generating, from an output image, a segmentation mask having areas occupied by individual tumors in the output image marked in the segmentation mask;
- computing statistics for each tumor marked in the segmentation mask; and
- applying a filter to the statistics of the tumors to edit the segmentation mask, wherein application of the filter selects and deselects tumors according to the filter to edit the segmentation mask to remove insignificant tumors;
- wherein the method further comprises:
  - creating a visualization of the histological image in accordance with the edited segmentation mask;

receiving a selection of an individual tumor in the edited segmentation mask; and executing an additional computational diagnostic process on the selected individual tumor.

9. A non-transitory computer readable medium having stored thereon computer executable instructions which, when executed by a processor, cause the processor to perform a method for identifying tumors in a histological image, the method comprising:

generating, from an output image, a segmentation mask having areas occupied by individual tumors in the output image marked in the segmentation mask;

computing statistics for each tumor marked in the segmentation mask; and applying a filter to the statistics of the tumors to edit the segmentation mask, wherein application of the filter selects and deselects tumors according to the filter to edit the segmentation mask to remove insignificant tumors;

wherein:

the output image comprises an array of pixels, each pixel in the output image being assigned to one of a plurality of tissue classes;

the output image is generated by a convolutional neural network based on the histological image by performing acts comprising:

extracting image patches from the histological image, the image patches being area portions of the histological image having a size defined by numbers of pixels in width and height;

providing the convolutional neural network with a set of weights and a plurality of channels, each channel corresponding to one of the plurality of tissue classes;

inputting each image patch as an input image patch into the convolutional neural network;

performing multi-stage convolution to generate convolution layers of ever decreasing dimensions up to and including a final convolution layer of minimum dimensions, followed by multi-stage transpose convolution to reverse the convolutions by generating deconvolution layers of ever increasing dimensions until a layer is recovered matched in size to the input image patch, each pixel in the recovered layer containing a probability of belonging to each of the tissue classes; and assigning the tissue class to each pixel of the recovered layer based on said probabilities to arrive at an output image patch.

10. The computer readable medium of claim 9, wherein the method further comprises:

providing the convolutional neural network with at least one skip connection, each of which takes intermediate results from at least one of the convolution layers of larger dimensions than the final convolution layer and subjects those results to as many transpose convolutions as needed, which may be none, one or more than one, to obtain at least one further recovered layer matched in size to the input image patch; and prior to said step of assigning a tissue class to each pixel, further processing the recovered layer to combine it with the at least one further recovered layers in order to recompute the probabilities to take account of the at least one skip connection.

11. A non-transitory computer readable medium having stored thereon computer executable instructions which, when executed by a processor, cause the processor to perform a method for identifying tumors in a histological image, the method comprising:

generating, from an output image, a segmentation mask having areas occupied by individual tumors in the output image marked in the segmentation mask;

computing statistics for each tumor marked in the segmentation mask; and applying a filter to the statistics of the tumors to edit the segmentation mask, wherein application of the filter selects and deselects tumors according to the filter to edit the segmentation mask to remove insignificant tumors;

wherein the histological image is a composite including a plurality of histological images obtained from differently stained, adjacent sections of a region of tissue.

12. A non-transitory computer readable medium having stored thereon computer executable instructions which, when executed by a processor, cause the processor to perform a method for identifying tumors in a histological image, the method comprising:

generating, from an output image, a segmentation mask having areas occupied by individual tumors in the output image marked in the segmentation mask;

computing statistics for each tumor marked in the segmentation mask; and applying a filter to the statistics of the tumors to edit the segmentation mask, wherein application of the filter selects and deselects tumors according to the filter to edit the segmentation mask to remove insignificant tumors;

wherein the method further comprises:

creating a visualization of the histological image in accordance with the edited segmentation mask;

receiving a selection of an individual tumor in the edited segmentation mask; and executing an additional computational diagnostic process on the selected individual tumor.

\* \* \* \* \*